US009850492B2

(12) United States Patent
Ishiguro et al.

(10) Patent No.: US 9,850,492 B2
(45) Date of Patent: Dec. 26, 2017

(54) APTAMER TO IL-17 AND USE THEREOF

(71) Applicants: THE UNIVERSITY OF TOKYO, Tokyo (JP); ZENYAKU KOGYO KABUSHIKI KAISHA, Tokyo (JP)

(72) Inventors: Akira Ishiguro, Tokyo (JP); Yoshikazu Nakamura, Tokyo (JP); Kazuhiko Haruta, Tokyo (JP); Natsuki Otaki, Tokyo (JP)

(73) Assignees: The University of Tokyo, Tokyo (JP); Zenyaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/777,471

(22) PCT Filed: Mar. 20, 2014

(86) PCT No.: PCT/JP2014/057919
§ 371 (c)(1),
(2) Date: Sep. 15, 2015

(87) PCT Pub. No.: WO2014/148638
PCT Pub. Date: Sep. 25, 2014

(65) Prior Publication Data
US 2016/0046944 A1 Feb. 18, 2016

(30) Foreign Application Priority Data
Mar. 22, 2013 (JP) .................................. 2013-060817

(51) Int. Cl.
| A61K 31/70 | (2006.01) |
| C07H 21/02 | (2006.01) |
| C07H 21/04 | (2006.01) |
| C12N 15/115 | (2010.01) |
| A61K 31/7088 | (2006.01) |
| A61K 45/06 | (2006.01) |
| G01N 33/68 | (2006.01) |
| C07K 14/54 | (2006.01) |
| C12N 5/00 | (2006.01) |

(52) U.S. Cl.
CPC ........ *C12N 15/115* (2013.01); *A61K 31/7088* (2013.01); *A61K 45/06* (2013.01); *C07K 14/54* (2013.01); *G01N 33/6869* (2013.01); *C12N 2310/16* (2013.01); *C12N 2310/315* (2013.01); *C12N 2310/321* (2013.01); *C12N 2310/322* (2013.01); *C12N 2310/3231* (2013.01); *C12N 2310/344* (2013.01); *C12N 2310/3521* (2013.01); *C12N 2310/3533* (2013.01); *C12N 2320/30* (2013.01); *G01N 2333/54* (2013.01)

(58) Field of Classification Search
None
See application file for complete search history.

(56) References Cited

U.S. PATENT DOCUMENTS

| 8,440,801 B2 | 5/2013 | Nakamura et al. |
| 2004/0137010 A1 | 7/2004 | Wilson et al. |
| 2005/0260651 A1 | 11/2005 | Calias et al. |
| 2006/0193821 A1 | 8/2006 | Diener et al. |
| 2009/0170219 A1 | 7/2009 | Nakamura et al. |
| 2010/0256038 A1 | 10/2010 | Curnock |
| 2011/0177578 A1 | 7/2011 | Nakamura et al. |

FOREIGN PATENT DOCUMENTS

| CA | 2 596 509 A1 | 8/2006 |
| CN | 101537189 A | 9/2009 |
| EP | 1938802 A1 | 7/2008 |
| JP | 2006-506055 A | 2/2006 |
| JP | 2007-527246 A | 9/2007 |
| WO | WO 91/19813 A1 | 12/1991 |
| WO | WO 94/08050 A1 | 4/1994 |
| WO | WO 95/07364 A1 | 3/1995 |
| WO | WO 2006/088925 A2 | 8/2006 |
| WO | WO 2007/004748 A1 | 1/2007 |
| WO | WO 2007/035922 A2 | 3/2007 |
| WO | WO 2008/028081 A2 | 3/2008 |
| WO | WO 2010/008001 A1 | 1/2010 |

OTHER PUBLICATIONS

Adachi et al., *Biochimie*, 93: 1081-1088 (2011).
Chen et al., *Osteoarthritis and Cartilage*, 19(6) 711-718 (2011).
Ishiguro et al., *Arthritis and Rheumatism*, 63(2): 455-466 (2011).
Karlsen et al., *Nucleic Acid Therapeutics*, 22(6): 366-370 (2012).
Nakamura et al., *Genes to Cells*, 17: 344-364 (2012).
Lanfranchi et al., *Genome Research*, 6(1): 35-42 (1996).
Zhou et al., *Cytokine*, 38(3): 157-164 (2007).
Canadian Patent Office, Office Action in Canadian Patent Application No. 2,730,796 (dated Jul. 23, 2012).
European Patent Office, Supplementary European Search Report issued in European Patent Application No. 09 79 7926 (dated Dec. 11, 2012).
Japanese Patent Office, International Search Report in International Patent Application No. PCT/JP2009/062764 (dated Oct. 13, 2009).

(Continued)

*Primary Examiner* — Sean McGarry
(74) *Attorney, Agent, or Firm* — Leydig, Voit & Mayer, Ltd.

(57) ABSTRACT

The present invention provides an aptamer that binds to IL-17 to inhibit binding of IL-17 and IL-17 receptor; a complex containing the aptamer and a functional substance (e.g., affinity substance, labeling substance, enzyme, drug delivery medium, drug and the like); a medicament containing the aptamer, or a complex containing the aptamer and a functional substance, a diagnosing drug and labeling agent and the like.

21 Claims, 4 Drawing Sheets

(56) References Cited

OTHER PUBLICATIONS

Japanese Patent Office, International Search Report in International Patent Application No. PCT/JP2014/057919 (dated Jun. 24, 2014).
Chinese Patent Office, First Office Action in Chinese Patent Application No. 201480017486.8 (dated Dec. 5, 2016).

Structure of representative 5'-PEG
form (two kinds of linkers)

Structure of representative both
5',3'-PEG form

Suppressing effect on mouse IL-23-induced psoriasis model

A

B

Arthritis suppressing effect on glucose-6-phosphate isomerase-induced arthritis model in mice Arthritis onset suppressing effect on collagen-induced arthritis model in mice

A

B

APTAMER TO IL-17 AND USE THEREOF

CROSS-REFERENCE TO RELATED APPLICATIONS

This patent application is the U.S. national phase of International Patent Application No. PCT/JP2014/057919, filed Mar. 20, 2014, which claims the benefit of Japanese Patent Application No. 2013-060817, filed on Mar. 22, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 270,748 bytes ASCII (Text) file named "721887ReplacementSequenceListing-2$^{nd}$" created Nov. 1, 2017.

TECHNICAL FIELD

The present invention relates to an aptamer against interleukin (IL-17), a method of utilizing the same, and the like.

BACKGROUND ART

IL-17 (or CTLA-8), a cytokine secreted by Th17 cells and the like, is profoundly associated with inflammatory diseases, autoimmune diseases, and infectious diseases. Human IL-17 is a 20-30 kDa glycoprotein, constituted of 155 amino acids, comprising a signal peptide at the N-terminus. In the molecular structure thereof, six cysteine residues and one N-binding sugar chain binding site are present. The mature form consists of 136 amino acids, normally occurring as a dimer.

As proteins of the IL-17 family, six kinds of proteins are known: IL-17A, B, C, D, E, and F. Generally, IL-17 refers IL-17A. IL-17E is also called IL-25. The amino acid sequence homology of human IL-17 to human IL-17B, C, D, E, and F is 25, 28, 22, 27, and 44%, respectively, IL-17F being of the highest homology. Human IL-17 has a homology of 63% to mouse IL-17. As receptors thereof, IL-17RA, IL-17RB, IL-17RC, IL-17RD, and IL-17RE are known. IL-17 and IL-17F form a homodimer or heterodimer and bind to IL-17RA and IL-17RC. The binding of IL-17 and IL-17RA is weak at a Kd value of about $10^{-7}$, and involvement of IL-17RC may be important.

The Th17 cells are CD4$^+$ T cells that produce IL-17. When Th17 cells are stimulated with IL-23 in vitro, IL-17 production is induced. Meanwhile, TGF-β and IL-6 play an important role in the differentiation induction of Th17 cells. TGF-β and IL-6 act on naïve T cells to induce the expression of RORγt (transcription factor). Because a deficiency in RORγt prevents Th17 cells from being differentiated, and also because naïve T cells can conversely be differentiated into IL-17-producing cells by forcedly expressing RORγt, this transcription factor is thought to be important to the differentiation of Th17 cells. Although activation of STAT3 by IL-6 is important to the induction of the expression of RORγt, activation of STAT5 by IL-2 conversely suppresses the expression. IL-2 is necessary for the differentiation of regulatory T cells; IL-2-deficient mice show serious autoimmunity; this is thought to be due to a decrease in regulatory T cells along with over-differentiation of Th17 cells. When naïve T cells are stimulated with TGF-β alone in vitro, not Th17, but regulatory T cells, are induced. IFN-γ produced by Th1 cells, IL-4 produced by Th2 cells, and the like act suppressively on the differentiation of Th17 cells.

When IL-17 binds to an IL-17 receptor, the NF-κB pathway, MAP kinase pathway, and C/EBP pathway are activated via Act-1 and TRAF6, resulting in the induction of inflammatory cytokines and chemokines. For example, IL-17 acts on macrophages to induce the expression of IL-1, TNF and the like. In addition, IL-17 is known to act also on connective tissue cells and epithelial tissue cells such as fibroblasts and endothelial cells, and on immune system cells such as dendritic cell progenitors, to induce the expression of various receptors and cytokines such as IL-6 and IL-1.

Cytokines such as TNF-α, IL-1β, and IL-6 are involved in the production of IL-17. Meanwhile, production of these cytokines is induced by IL-17. IL-17 is known to act synergistically with other cytokines.

It has been found that IL-17 is profoundly associated with inflammatory diseases, autoimmune diseases and the like. It is known that the expression of IL-17 is elevated in patients with rheumatoid arthritis, age-related macular degeneration, psoriasis, systemic lupus erythematosus, Behçet's disease, graft rejection, nephritic syndrome, inflammatory bowel disease, asthma, multiple sclerosis, periodontal disease and the like. In IL-17-deficient mice, it has been reported that collagen-induced arthritis (CIA), which is a model of rheumatoid arthritis; experimental autoimmune encephalomyelitis (EAE), which is a model of multiple sclerosis; contact type hypersensitivity reactions by DNFB or TNCB; delayed type hypersensitivity reactions by methylated BSA; airway hypersensitive reactions by OVA induction, and the like are remarkably suppressed.

IL-17 is also associated with cancers. It has been reported that subcutaneous transplantation of non-small cell lung cancer cells to SCID mice promotes the proliferation of cancer cells in mice having IL-17 expressed highly therein. It has also been reported that IL-17 is also associated with cervical cancer and ovarian cancer.

IL-17 is associated with infectious diseases. IL-17 receptor knockout mice are highly susceptible to *Klebsiella pneumoniae* infection, *Candida albicans* infection, *Toxsoplasma gondii* infection and the like. IL-17 production is induced by lipopolysaccharides (LPS) and bacterial cell body components such as of *Borrelia burgdorferi* and *Klebsiella pneumoniae*. These components are thought to promote IL-17 production by acting on antigen-presenting cells to induce IL-23. In IL-17R-knockout mice, after *Klebsiella pneumoniae* infection, in infected sites in the lung, the production of CXCL1, CXCL2, G-CSF and the like, which play an important role in the migration and functions of neutrophils, is reduced and the migration of neutrophils is suppressed.

In recent years, applications of RNA aptamers to therapeutic drugs, diagnostic reagents, and test reagents have been drawing attention; some RNA aptamers have already been in clinical study stage or in practical use. In December 2004, the world's first RNA aptamer drug, Macugen, was approved as a therapeutic drug for age-related macular degeneration in the US. An RNA aptamer refers to an RNA that binds specifically to a target molecule such as a protein, and can be prepared using the SELEX (Systematic Evolution of Ligands by Exponential Enrichment) method (cf. Patent document 1, 2, and 3). In the SELEX method, an RNA that binds specifically to a target molecule is selected from an RNA pool with about $10^{14}$ different nucleotide sequences. The RNA used has a random sequence of about 40 residues, which is flanked by primer sequences. This RNA pool is allowed to mix with a target molecule, and only the RNA that has bound to the target molecule is collected using a filter and the like. The RNA collected is amplified by RT-PCR, and this is used as a template for the next round. By repeating this operation about 10 times, an RNA aptamer that binds specifically to the target molecule can be obtained.

Aptamer drugs, like antibody drugs, can target extracellular factors. With reference to many scientific papers and other reference materials in the public domain, there is a possibility that aptamer drugs surpass antibody drugs in some aspects. For example, aptamers often show higher binding force and higher specificity than antibodies do. Aptamers are unlikely to undergo immune elimination, and adverse reactions which are characteristic of antibodies and result from antibody-dependent cell-mediated cytotoxicity (ADCC) and complement-dependent cytotoxicity (CDC), do not occur with the use of aptamers. From the aspect of delivery, since aptamers are about 1/10 of antibody in size, delivery of a drug to the object site is easier. Since aptamers are produced by chemical synthesis, various modifications can be done easily, and reduction of cost by large-scale production is possible. Meanwhile, the blood half-lives of aptamers are generally shorter than those of antibodies; however, this property is sometimes advantageous in view of toxicity. These facts lead to the conclusion that even when the same molecule is targeted, aptamer drugs potentially surpass antibody drugs.

Patent document 4 describes an aptamer obtained by the above-mentioned SELEX method, which binds to IL-17 to inhibit binding of IL-17 and IL-17 receptor.

DOCUMENT LIST

Patent Documents patent document 1: WO91/19813
patent document 2: WO94/08050
patent document 3: WO95/07364
patent document 4: WO2010/008001

SUMMARY OF THE INVENTION

Problems to be Solved by the Invention

The present invention is directed to provision of an aptamer against IL-17 and a method for utilizing the same, and the like. Particularly, the present invention aims to provide an aptamer with higher quality which is suitable for use as a pharmaceutical product.

Means of Solving the Problems

The present inventors have conducted intensive studies in an attempt to solve the aforementioned problems and successfully produced an anti-IL-17 aptamer having an extremely high quality and a remarkably high binding inhibitory activity against IL-17 and IL-17 receptor as compared to conventionally-known anti-IL-17 aptamers, and capable of inhibiting the physiological activity of IL-17, which resulted in the completion of the present invention.

Accordingly, the present invention is as follows:

[1] an aptamer comprising a sequence represented by the following formula (Ia), which binds to IL-17 to inhibit binding of IL-17 and IL-17 receptor:

g(M)g(M)g(M)u(M)a'(M)g'($X_1$)c(M)c(M)g'g(M)a'($X_4$)g ($X_5$)g(M)a(M)g($X_5$)u'(F)c($X_7$)a'($X_2$)g($X_6$)u'(F)r($X_3$)a' ($X_3$)u(M)c(M)g(M)g(M)u'($X_7$)a'(M)c'(M)c'(M)c'(M) (SEQ ID NO: 95)

wherein a, g, c and u are each an RNA wherein the base is adenine, guanine, cytosine and uracil, respectively, r is an RNA wherein the base is adenine or guanine, a', g' and c' are each an RNA or DNA wherein the base is adenine, guanine and cytosine, respectively, u' is an RNA wherein the base is uracil, a DNA wherein the base is uracil or a DNA wherein the base is thymine, parentheses in nucleotide indicate modification of the nucleotide, (M) indicates that, when the nucleotide is an RNA, a hydroxyl group at the 2'-position of ribose therein is substituted by an O-methyl group, (F) indicates that, when the nucleotide is an RNA, a hydroxyl group at the 2'-position of ribose therein is substituted by a fluorine atom, ($X_1$) indicates that nucleotide is non-modified or phosphorothioated, or when the nucleotide is an RNA, a hydroxyl group at the 2'-position of ribose therein is substituted by a fluorine atom, ($X_2$) indicates that nucleotide is non-modified, or when the nucleotide is an RNA, a hydroxyl group at the 2'-position of ribose therein is substituted by a fluorine atom, ($X_3$) indicates that nucleotide is non-modified, or when the nucleotide is an RNA, a hydroxyl group at the 2'-position of ribose therein is substituted by an O-methyl group, ($X_4$) indicates that nucleotide is non-modified, or when the nucleotide is an RNA, a hydroxyl group at the 2'-position of ribose therein is substituted by a fluorine atom or an O-methyl group, ($X_5$) indicates that nucleotide is non-modified or phosphorothioated, ($X_6$) indicates that nucleotide is non-modified or phosphorothioated, or when the nucleotide is an RNA, a hydroxyl group at the 2'-position of ribose therein is substituted by an O-methyl group, and ($X_7$) indicates that when nucleotide is an RNA, a hydroxyl group at the 2'-position of ribose therein is substituted by a fluorine atom or an O-methyl group;

[2] the aptamer of the above-mentioned [1], comprising a sequence represented by the following formula (Ia'):

g(M)g(M)g(M)u(M)a'(M)g'($X_5$)c(M)c(M)Gg(M)a($X_4$)gg (M)a(M)g($X_5$)u'(F)c($X_7$)a'($X_2$)g($X_5$)u'(F)r($X_3$)a($X_3$)u(M) c(M)g(M)g(M)u($X_7$)a(M)c'(M)c'(M)c'(M) (SEQ ID NO: 96)

wherein a, g, c, u and r, a', c' and u', as well as (M), (F) and ($X_2$)-($X_5$) and ($X_7$) are as defined for the formula (Ia), and G is a DNA wherein the base is guanine;

[3] the aptamer of the above-mentioned [1], comprising a sequence represented by the following formula (I):

g(M)g(M)g(M)u(M)a'(M)g'($X_1$)c(M)c(M)g'g(M)a'($X_2$)gg (M)a(M)gu'(F)c(F)a'($X_2$)gu'(F)a($X_3$)a'($X_3$)u(M)c(M)g (M)g(M)u'(F)a'(M)c'(M)c'(M)c'(M) (SEQ ID NO: 97)

wherein a, g, c and u, a', g', c' and u', as well as (M), (F) and ($X_1$)-($X_3$) are as defined for the formula (Ia);

[4] the aptamer of the above-mentioned [1], comprising a sequence represented by the following formula (Ia"):

g(M)g(M)g(M)u(M)a'(M)g($X_5$)c(M)c(M)Gg(M)a($X_7$)g($X_5$)
g(M)a(M)g($X_5$)u'(F)c($X_7$)a(F)g($X_6$)u'(F)r($X_3$)a($X_3$)u(M)
c(M)g(M)g(M)u($X_7$)a'(M)c'(M)c'(M)c'(M) (SEQ ID NO: 98)

wherein a, g, c, u and r, a', c' and u', as well as (M), (F), ($X_3$) and ($X_5$)-($X_7$) are as defined for the formula (Ia), and
G is a DNA wherein the base is guanine;

[5] the aptamer of the above-mentioned [4], wherein, in the formula (Ia"), c'(M)c'(M)c'(M) on the 3'-terminal side is c(M)c(M)c(M);

[6] the aptamer of any of the above-mentioned [1]-[5], wherein a nucleotide wherein, when it is an RNA, a hydroxyl group at the 2'-position of ribose therein is optionally substituted by an O-methyl group and the base is guanine is added to the 5'-terminus of the sequence represented by the formula (Ia), (Ia'), (I) or (Ia"), and/or a nucleotide wherein the base is cytosine is added to the 3'-terminus thereof;

[7] the aptamer of the above-mentioned [1], comprising the sequence of any of SEQ ID NOs: 52-94;

[8] the aptamer of the above-mentioned [3], comprising the sequence of any of SEQ ID NOs: 3-49;

[9] the aptamer of any of the above-mentioned [1]-[8], having a base length of not more than 70;

[10] an aptamer comprising a sequence represented by the following formula (II), which binds to IL-17 to inhibit binding of IL-17 and IL-17 receptor:

g($x_1$)g($x_1$)g($x_1$)u(F)ag(S)c(F)c(F)g'(S)g($x_2$)aggagu(F)c(F)
agu(F)aau(F)c(F)ggu(F)ac'($x_3$)c'($x_3$)c'($x_3$) (SEQ ID NO: 99)

wherein
a, g, c and u are each an RNA wherein the base is adenine, guanine, cytosine and uracil, respectively,
g' and c' are each an RNA or DNA wherein the base is guanine or cytosine, respectively, parentheses in nucleotide indicate modification of the nucleotide,
(F) indicates that a hydroxyl group at the 2'-position of ribose in the nucleotide is substituted by a fluorine atom,
(S) indicates that, when nucleotide is an RNA, it is phosphorothioated,
($x_1$) indicates that nucleotide is modified with Locked Nucleic Acid (LNA), or when the nucleotide is an RNA, a hydroxyl group at the 2'-position of ribose therein is substituted by an O-methyl group,
($x_2$) indicates that nucleotide is non-modified, or when the nucleotide is an RNA, a hydroxyl group at the 2'-position of ribose therein is substituted by an O-methyl group, and
($x_3$) indicates that nucleotide is non-modified, or modified with LNA;

[11] the aptamer of the above-mentioned [10], comprising the sequence shown by SEQ ID NO: 1 or SEQ ID NO: 2;

[12] the aptamer of the above-mentioned [10] or [11], having a base length of not more than 70;

[13] the aptamer of any of the above-mentioned [1]-[12], which is modified with inverted dT or polyethylene glycol (PEG);

[14] the aptamer of the above-mentioned [13], wherein the inverted dT or polyethylene glycol is bound to the 5'-terminus and/or the 3'-terminus of the aptamer;

[15] a complex comprising the aptamer of any of [1]-[14] and a functional substance;

[16] the complex of [15], wherein the functional substance is an affinity substance, a substance for labeling, an enzyme, a drug delivery vehicle or a drug;

[17] a medicament comprising the aptamer of any of [1]-[14] or the complex of [15] or [16];

[18] a medicament for the treatment or prophylaxis of a disease including inflammatory disease, autoimmune disease, cancer, allergy, infection and the like, comprising the aptamer of any of [1]-[14] or the complex of [15] or [16];

[19] a diagnostic reagent comprising the aptamer of any of [1]-[14] or the complex of [15] or [16];

[20] a detection probe comprising the aptamer of any of [1]-[14] or the complex of [15] or [16];

[21] a carrier for IL-17 purification, comprising the aptamer of any of [1]-[14] or the complex of [15] or [16];

[22] a method of detecting IL-17, comprising using the aptamer of any of [1]-[14] or the complex of [15] or [16]; and

[23] a method of purifying IL-17, comprising using the aptamer of any of [1]-[14] or the complex of [15] or [16].

Effect of the Invention

The aptamer or the complex of the present invention can be useful as a medicament or reagent such as a diagnostic reagent for a disease including inflammatory disease, autoimmune disease, cancer, allergy or infection, and the like. The aptamer or the complex of the present invention can also be useful in purifying and concentrating IL-17, labeling of IL-17, and detecting and quantifying IL-17.

DESCRIPTION OF EMBODIMENTS

Figure 1:
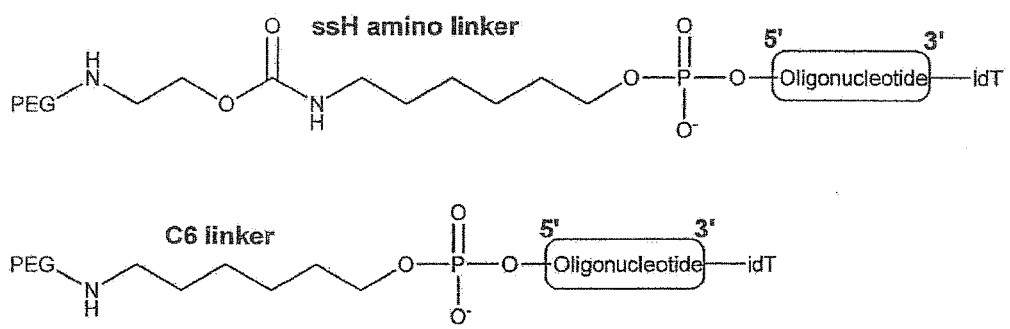
FIG. 1 shows the structure of a representative 5'-terminus-modified pegylated aptamer when the aptamer of the present invention is pegylated via a linker, and the structure of a 5'-terminus- and 3'-terminus-modified pegylated aptamer.
Figure 1:
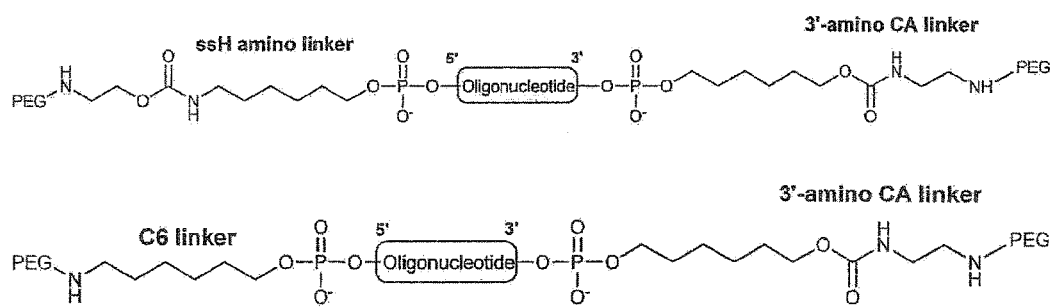

In the first embodiment, the present invention provides an aptamer comprising a sequence represented by the following formula (Ia), which binds to IL-17 to inhibit binding of IL-17 and IL-17 receptor:

g(M)g(M)g(M)u(M)a'(M)g'($X_1$)c(M)c(M)g'g(M)a'($X_4$)g($X_5$)g(M)a(M)g($X_5$)u'(F)c($X_7$)a'($X_2$)g($X_6$)u'(F)r($X_3$)a'($X_3$)u(M)c(M)g(M)g(M)u'($X_7$)a'(M)c'(M)c'(M)c'(M) (SEQ ID NO: 95)

wherein a, g, c and u are each an RNA wherein the base is adenine, guanine, cytosine and uracil, respectively, r is an RNA wherein the base is adenine or guanine, a', g' and c' are each an RNA or DNA wherein the base is adenine, guanine and cytosine, respectively, u' is an RNA wherein the base is uracil, a DNA wherein the base is uracil or a DNA wherein the base is thymine, parentheses in nucleotide indicate modification of the nucleotide, (M) indicates that, when the nucleotide is an RNA, a hydroxyl group at the 2'-position of ribose therein is substituted by an O-methyl group, (F) indicates that, when the nucleotide is an RNA, a hydroxyl group at the 2'-position of ribose therein is substituted by a fluorine atom, ($X_1$) indicates that nucleotide is non-modified or phosphorothioated, or when the nucleotide is an RNA, a hydroxyl group at the 2'-position of ribose therein is substituted by a fluorine atom, ($X_2$) indicates that nucleotide is non-modified, or when the nucleotide is an RNA, a hydroxyl group at the 2'-position of ribose therein is substituted by a fluorine atom, ($X_3$) indicates that nucleotide is non-modified, or when the nucleotide is an RNA, a hydroxyl group at the 2'-position of ribose therein is substituted by an O-methyl group, ($X_4$) indicates that nucleotide is non-modified, or when the nucleotide is an RNA, a hydroxyl group at the 2'-position of ribose therein is substituted by a fluorine atom or an O-methyl group, ($X_5$) indicates that nucleotide is non-modified or phosphorothioated, ($X_6$) indicates that nucleotide is non-modified or phosphorothioated, or when the nucleotide is an RNA, a hydroxyl group at the 2'-position of ribose therein is substituted by an O-methyl group, ($X_7$) indicates that when nucleotide is an RNA, a hydroxyl group at the 2'-position of ribose therein is substituted by a fluorine atom or an O-methyl group.

In a preferable embodiment, the present invention provides an aptamer comprising a sequence represented by the following formula (Ia'), which binds to IL-17 to inhibit binding of IL-17 and IL-17 receptor:

g(M)g(M)g(M)u(M)a'(M)g($X_5$)c(M)c(M)Gg(M)a($X_4$)gg(M)a(M)g($X_5$)u'(F)c($X_7$)a($X_2$)g($X_5$)u'(F)r($X_3$)a($X_3$)u(M)c(M)g(M)g(M)u($X_7$)a(M)c'(M)c'(M)c'(M) (SEQ ID NO: 96)

wherein a, g, c, u and r, a', c' and u', as well as (M), (F) and ($X_2$)-($X_5$) and ($X_7$) are as defined for the formula (Ia), and G is a DNA wherein the base is guanine.

In a preferable embodiment, the present invention provides an aptamer comprising a sequence represented by the following formula (I), which binds to IL-17 to inhibit binding of IL-17 and IL-17 receptor:

g(M)g(M)g(M)u(M)a'(M)g'($X_1$)c(M)c(M)g'g(M)a'($X_2$)gg(M)a(M)gu'(F)c(F)a'($X_2$)gu'(F)a($X_3$)a'($X_3$)u(M)c(M)g(M)g(M)u'(F)a'(M)c'(M)c'(M)c'(M) (SEQ ID NO: 97)

wherein a, g, c and u, a', g', c' and u', as well as (M), (F) and ($X_1$)-($X_3$) are as defined for the formula (Ia).

In a preferable embodiment, moreover, the present invention provides an aptamer comprising a sequence represented by the following formula (Ia''), which binds to IL-17 to inhibit binding of IL-17 and IL-17 receptor:

g(M)g(M)g(M)u(M)a'(M)g($X_5$)c(M)c(M)Gg(M)a($X_7$)g($X_5$)g(M)a(M)g($X_5$)u'(F)c($X_7$)a(F)g($X_6$)u'(F)r($X_3$)a($X_3$)u(M)c(M)g(M)g(M)u($X_7$)a'(M)c'(M)c'(M)c'(M) (SEQ ID NO: 98)

wherein a, g, c, u and r, a', c' and u', as well as (M), (F), ($X_3$) and ($X_5$)-($X_7$) are as defined for the formula (Ia), and G is a DNA wherein the base is guanine.

In a preferable embodiment, moreover, the present invention provides an aptamer which binds to IL-17 to inhibit binding of IL-17 and IL-17 receptor, wherein, in the formula (Ia''), c'(M)c'(M)c'(M) on the 3'-terminal side is c(M)c(M)c(M).

An aptamer refers to a nucleic acid molecule having a binding activity for a particular target molecule. The aptamer can inhibit the activity of a particular target molecule by binding to the particular target molecule. The aptamer of the present invention may be an RNA, a DNA, a modified nucleic acid or a mixture thereof. The aptamer of the present invention can also be in a linear or cyclic form.

IL-17 refers to a cytokine secreted by Th17 cells and the like, and is, for example, a protein having the amino acid sequence shown by Accession code AAH67505 or NP002181. IL-17 is sometimes called IL-17A or CTLA-8. In addition to being produced in animal bodies, IL-17 as used in the present invention can be produced by using mouse and other mammalian cells, insect cells, cells of *Escherichia coli* and the like, and can also be prepared by chemical synthesis. When IL-17 is prepared by cell culture or chemical synthesis, a mutant can easily be prepared. Here, a mutant means a sequence wherein several amino acids have been substituted or a partial amino acid sequence, and means a protein or peptide having at least one of the activities essentially possessed by IL-17. When an amino acid is substituted, the substituent amino acid may be a naturally occurring amino acid, or may be a non-naturally occurring amino acid. As mentioned in the present invention, IL-17 includes these mutants.

An IL-17 receptor means a cell surface protein to which IL-17 binds and a protein that mediates intracellular signaling. As members of the IL-17 receptor family, IL-17RA, IL-17RB, IL-17RC, IL-17RD, and IL-17RE are known. As mentioned in the present invention, the IL-17 receptor may be a protein comprising a naturally occurring amino acid sequence, or may be a mutant thereof. Here, a mutant means a sequence wherein several amino acids have been substituted or a partial amino acid sequence, and means a protein or peptide possessing binding activity for IL-17. The aptamer of the present invention inhibits the binding of IL-17 and IL-17 receptor.

Whether the aptamer of the present invention inhibits binding of IL-17 and IL-17 receptor can be evaluated, for example, by the following test.

For the measurement, BIAcore2000 or T100 manufactured by BIAcore is used. Protein A (21181, PIERCE) is immobilized on a CM5 sensor chip, and a protein wherein IL-17 receptor and Fc portion of IgG are fused (e.g., recombinant human IL-17R-Fc chimera (177-IR, R&D systems)) is immobilized thereon. The amount to be immobilized is about 20 (for 2000) or about 1200RU. As an analyte, IL-17 (about 100 or 150 nM) and an aptamer (about 50 or 100 nM) are mixed, maintained for 15 min and the mixture is injected into BIAcore2000. The binding of IL-17 to IL-17 receptor is detected.

As the value becomes lower, the aptamer is judged to more strongly inhibit the binding of IL-17 and IL-17 receptor.

In a preferable embodiment, the aptamer of the present invention binds to IL-17 to inhibit binding of IL-17 and IL-17 receptor, whereby it can inhibit a signaling activity of IL-17 derived from any mammal. Examples of the mammal include primates (e.g., humans, monkeys), rodents (e.g., mice, rats, guinea pigs), and companion animals, domestic animals and work animals (e.g., dogs, cats, horses, cattles, goats, sheep, pigs).

Inhibition of IL-17 signaling activity means an inhibitory capacity against any signaling activity that IL-17 has. For example, IL-17 is known to bind to IL-17 receptor, and activates NF-κB pathway and MAP kinase pathway via TRAF6 and the like, and then production of various cytokines and chemokines is induced via such signal transduction pathways. Therefore, the IL-17 signaling inhibitory activity refers to an activity that inhibits the production of these cytokines, chemokines and the like, that are present at the downstream of the IL-17 signal transduction pathway. Since the expression of these cytokines and chemokines induces the migration and activation of inflammatory cells, signaling inhibitory activity against IL-17 also means inhibition of the activities thereof.

In the aptamer of the present invention, a part of nucleotide is modified as shown in the above-mentioned formulas (Ia), (Ia'), (I) and (Ia") to enhance binding property to IL-17, binding inhibitory activity against IL-17 and IL-17 receptor, and the like.

In the present specification, nucleotide being non-modified means that a hydroxyl group at the 2'-position of ribose in a ribonucleotide, or hydrogen at the 2'-position of ribose in a deoxyribonucleotide is not substituted by other element, and nucleotide being modified means, for example, that a hydroxyl group at the 2'-position of ribose in a ribonucleotide is substituted by a fluorine atom or an O-methyl group, nucleotide is phosphorothioated, modified with Locked Nucleic Acid (LNA) and the like. The "nucleotide is phosphorothioated" means that a phosphoric acid group in a binding site between adjacent nucleotides is sulfurated, that is, a phosphodiester bond is converted to a phosphorothioate bond, and being modified with LNA means that an oxygen atom at the 2'-position of ribose and a carbon atom at the 4'-position of nucleotide are methylene crosslinked.

Various modifications shown by the formulas (Ia), (Ia'), (I) and (Ia") can be performed according to a method known per se (e.g., Sproat et al., (1991), Nucl. Acid. Res. 19, 733-738; Cotton et al., (1991), Nucl. Acid. Res. 19, 2629-2635; Hobbs et al., (1973), Biochemistry 12, 5138-5145 and the like).

The present invention also provides an aptamer that binds to IL-17 to inhibit binding of IL-17 and IL-17 receptor, comprising a sequence wherein a nucleotide wherein, when it is an RNA, a hydroxyl group at the 2'-position of ribose therein is optionally substituted by an O-methyl group and the base is guanine is added to the 5'-terminus of the sequence represented by the formula (Ia), (Ia'), (I) or (Ia"), and/or a nucleotide wherein the base is cytosine is added to the 3'-terminus thereof.

Preferably, the aptamer of the present invention may be an aptamer containing a sequence selected from aptamer Nos. 3-49, and 52-94 shown below, or a conjugate of a plurality of such aptamers as long as it binds to IL-17 and inhibits the binding of IL-17 and IL-17 receptor.

In the above-mentioned conjugate of a plurality of such aptamers, conjugation can be achieved by tandem binding. In the conjugation, a linker may be utilized. As the linker, nucleotide chains (e.g., 1 to about 20 nucleotides) and non-nucleotide chains (e.g., —$(CH_2)_n$— linker, —$(CH_2CH_2O)_n$— linker, hexaethylene glycol linker, TEG linker, peptide-containing linker, —S—S— bond-containing linker, —CONH— bond-containing linker, —$OPO_3$— bond-containing linker) can be mentioned. The plurality as mentioned in the above-described plural conjugates not particularly limited, as long as it is two or more, and the plurality can be, for example, 2, 3 or 4.

The length of the aptamer of the present invention is not particularly limited, and can usually be not more than about 200 nucleotides. When the total number of nucleotides is smaller, chemical synthesis and mass-production will be easier, and there is a major advantage in terms of cost. It is also considered that chemical modification is easy, and stability in the body is high. Therefore, from the aspects of application to the use of a pharmaceutical product, the aptamer of the present invention more desirably has a shorter base length than 70 nucleotides, preferably not more than about 50 nucleotides, more preferably not more than about 40 nucleotides (e.g., not more than 40 nucleotides, not more than 39 nucleotides, not more than 38 nucleotides, not more than 37 nucleotides, not more than 36 nucleotides), most preferably not more than about 35 nucleotides (e.g., not more than 35 nucleotides, not more than 34 nucleotides, not more than 33 nucleotides).

In another embodiment, moreover, the present invention provides an aptamer comprising a sequence represented by the following formula (II), which binds to IL-17 to inhibit binding of IL-17 and IL-17 receptor:

$g(x_1)g(x_1)g(x_1)u(F)ag(S)c(F)c(F)g'(S)g(x_2)aggagu(F)c(F)agu(F)aau(F)c(F)ggu(F)ac'(x_3)c'(x_3)c'(x_3)$ (SEQ ID NO: 99)

wherein a, g, c and u are each an RNA wherein the base is adenine, guanine, cytosine and uracil, respectively, g' and c' are each an RNA or DNA wherein the base is guanine or cytosine, respectively, parentheses in nucleotide indicate modification of the nucleotide, (F) indicates that a hydroxyl group at the 2'-position of ribose in the nucleotide is substituted by a fluorine atom, (S) indicates that, when nucleotide is an RNA, it is phosphorothioated, ($x_1$) indicates that nucleotide is modified with LNA, or when the nucleotide is an RNA, a hydroxyl group at the 2'-position of ribose therein is substituted by an O-methyl group, ($x_2$) indicates that nucleotide is non-modified, or when the nucleotide is an RNA, a hydroxyl group at the 2'-position of ribose therein is substituted by an O-methyl group, and ($x_3$) indicates that nucleotide is non-modified, or modified with LNA.

Also, in an aptamer containing a sequence represented by the above-mentioned formula (II), nucleotide is partially modified as in the aptamer containing a sequence represented by the above-mentioned formula (Ia), (Ia'), (I) or (Ia"). The modification shown in the formula (II) can be performed according to a method known per se as mentioned above.

Preferably, the aptamer of the present invention may be an aptamer containing a sequence selected from aptamer No. 1 or 2 shown below, or a conjugate of a plurality of such aptamers as long as it binds to IL-17 and inhibits the binding of IL-17 and IL-17 receptor.

In the above-mentioned conjugate of a plurality of such aptamers, conjugation can be achieved by tandem binding. In the conjugation, a linker may be utilized. As the linker, nucleotide chains (e.g., 1 to about 20 nucleotides) and non-nucleotide chains (e.g., —(CH$_2$)$_n$— linker, —(CH$_2$CH$_2$O)$_n$— linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described plural conjugates not particularly limited, as long as it is two or more, and the plurality can be, for example, 2, 3 or 4.

In the aptamer of the present invention, nucleic acid base may be further altered (e.g., chemical substitution) to enhance binding property to IL-17, binding inhibitory activity against IL-17 and IL-17 receptor, stability, and the like. Such alteration includes that of 3'-terminus and 5'-terminus such as capping.

An alteration can further be performed by adding to an end a polyethyleneglycol, amino acid, peptide, inverted dT, nucleic acid, nucleosides, polynucleotide, Myristoyl, Lithocolic-oleyl, Docosanyl, Lauroyl, Stearoyl, Palmitoyl, Oleoyl, Linoleoyl, other lipids, steroids, cholesterol, caffeine, vitamins, pigments, fluorescent substances, anticancer agent, toxin, enzymes, radioactive substance, biotin and the like. For such alterations, see, for example, U.S. Pat. Nos. 5,660,985 and 5,756,703.

Particularly, when alteration is performed by terminal addition of PEG, the molecular weight of PEG is not particularly limited, and is preferably 1000-100000, more preferably 20000-90000. PEG may be linear or branched into two or more chains (multi-arm PEG). As for terminal addition of PEG, it may be added to only one of the 3'-terminus and 5'-terminus, or both of 3'-terminus and 5'-terminus.

Such PEG is not particularly limited, and those of ordinary skill in the art can appropriately select and use commercially available or known PEG (e.g., http://www.peg-drug.com/peg_product/branched.html). Specific preferable examples of PEG to be applied to the aptamer of the present invention include CS type PEG and GS type PEG (SUNBRIGHT ME-200GS manufactured by NOF CORPORATION) having a molecular weight of 20000, 2-branched GS type PEG having a molecular weight of 40000 (SUNBRIGHT GL2-400GS2 manufactured by NOF CORPORATION), 2-branched TS type PEG having a molecular weight of 40000 (SUNBRIGHT GL2-400TS manufactured by NOF CORPORATION), 4-branched TS type PEG having a molecular weight of 40000 (SUNBRIGHT GL4-400TS manufactured by NOF CORPORATION), 2-branched TS type PEG having a molecular weight of 80000 (SUNBRIGHT GL2-800TS manufactured by NOF CORPORATION), 4-branched TS type PEG having a molecular weight of 80000 (SUNBRIGHT GL4-800TS manufactured by NOF CORPORATION) and the like.

In this case, in the aptamer of the present invention, PEG may be directly added to the terminus. It is more preferable that a linker having a group which can bind to PEG and the like should be added to the terminus thereof, and PEG should be added to the aptamer of the present invention via the linker.

The linker for PEG and the aptamer of the present invention is not particularly limited, and carbon chain number, functional group and the like can be appropriately selected according to the binding site, the kind of PEG and the like. Examples of such linker include a linker having an amino group. Specifically, when added to the 5' terminus, ssH Linker (SAFC) or DMS(O)MT-AMINO-MODIFIER (GLEN RESEARCH) can be mentioned, and when added to the 3° terminus, TFA Amino C-6 lcaa CPG (ChemGenes) and the like can be mentioned. When this linker is selected, for example, an active group of N-hydroxysuccinimide is added to PEG, and reacted with an amino group on the linker side, whereby the aptamer of the present invention can be bound to PEG via the linker.

As PEG and linker, commercially available products can be preferably used. The reaction conditions and the like relating to the binding of PEG, a linker and the aptamer of the present invention can be appropriately determined by those of ordinary skill in the art.

The aptamer of the present invention can be chemically synthesized as disclosed herein and by a method known per se in the art. An aptamer binds to the target molecule in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target molecule can be substituted. In particular, because the region of stem structure has already formed base pairs and faces the inside of the double helical structure, nucleic acid bases are unlikely to bind directly to the target molecule. Therefore, even when a base pair is replaced with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change widely.

An aptamer can be prepared by utilizing the SELEX method or an improved version thereof (e.g., Ellington et al., (1990) Nature, 346, 818-822; Tuerk et al., (1990) Science, 249, 505-510). In the SELEX method, by increasing the number of rounds or using a competing substance, an aptamer exhibiting a stronger binding potential for the target molecule is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target molecule, but this does not mean binding to a bioactive site of the target molecule. Therefore, the aptamers obtained by SELEX do not necessarily act on the function of the target substance. IL-17 is a basic protein, and is thought to be likely to allow nucleic acids to bind thereto nonspecifically. An aptamer that does not bind to an active site does not affect the activity of the target substance. In fact, the RNA used for control did not inhibit the binding of IL-17 and IL-17 receptor.

The thus-selected active aptamer can be subjected to SELEX optimization to achieve high function. For SELEX optimization, a template wherein an aptamer with a determined sequence is partially randomized or a template doped with about 10 to 30% of random sequences is prepared, and SELEX is performed again.

An aptamer obtained by SELEX has a length of about 70 nucleotides, and this is not easy to prepare as a medicament as it is. Hence, it is necessary to repeat try-and-error efforts to shorten the aptamer to a length of about 50 nucleotides or less enabling easy chemical synthesis.

Depending on the primer design for an aptamer obtained by SELEX, the ease of the subsequent minimization operation changes. Unless an appropriate primer is designed, subsequent development will be impossible even if an aptamer with activity is selected by SELEX. In the present invention, an aptamer capable of maintaining the activity even with 31 nucleotides (aptamer Nos. 1-4, 6-15, 19-49, and 52-94) or 33 nucleotides (aptamer Nos. 5 and 16-18) can be obtained.

Aptamers are easily modifiable because they permit chemical synthesis. For aptamers, by predicting the secondary structure using the MFOLD program, or by predicting the conformation by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

When an important region for the binding of the obtained aptamer with the target molecule is identified by repeated try-and-error efforts as described above, the activity remains unchanged in many cases even when a new sequence is added to both ends of the sequence. The length of the new sequence is not particularly limited.

Modifications, like sequences, afford a wide range of design or alterations.

As stated above, aptamers permit a wide range of design or alterations. The present invention also provides a production method of aptamer that enables a wide range of design or alteration of an aptamer comprising a specified sequence (e.g., a sequence corresponding to a portion selected from among stem regions, internal loop regions, hairpin loop regions and single-strand regions: hereinafter, abbreviated as fixed sequence as required).

For example, the production method of such aptamer includes production of an aptamer comprising a fixed sequence by using a single kind of nucleic acid molecule consisting of a nucleotide sequence shown by:

TABLE 1

| Primer sequence (i) -(N)a-fixed sequence-(N)b- Primer sequence (ii) |
|---| wherein (N)a represents a nucleotide chain consisting of "a" units of N; (N)b represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be any numbers, and can be, for example, 1 to about 100, preferably 1 to about 50, more preferably 1 to about 30, still more preferably 1 to about 20 or 1 to about 10, or plural kinds of nucleic acid molecules (e.g., library of nucleic acid molecule different in the number of a, b etc.) and primer pairs corresponding to the primer sequences (i) and (ii), respectively.

The present invention also provides a complex comprising the aptamer of the present invention and a functional substance bound thereto. The bond between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly adds a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and Vero toxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction enzyme.

The aptamer or complex of the present invention can be used as, for example, a medicament, diagnostic drug, examination drug, or reagent. The same is particularly useful as a medicament, diagnostic drug, examination drug, or reagent for inflammation diseases, autoimmune diseases and the like.

Examples of the inflammatory diseases and autoimmune diseases and the like include multiple sclerosis (MS), systemic lupus erythematosus (SLE), ankylosing spondylitis (AS), Sjögren's syndrome, polymyositis (PM), dermatomyositis (DM), rheumatoid arthritis (RA), osteoarthritis (OA), inflammatory bowel disease (Crohn's disease and the like), systemic sclerosis (PSS), scleroderma, periarteritis nodosa (PN), thyroid gland disease (Graves' disease, Hashimoto's thyroiditis, and the like), Guillain-Barré syndrome, primary biliary cirrhosis (PBC), idiopathic thrombocytopenic purpura, autoimmune hemolytic anemia, myasthenia gravis (MG), amyotrophic lateral sclerosis (ALS), type I diabetes mellitus, plaque psoriasis, pustular psoriasis, asthma, neutrophil functional abnormalities, eosinophilic pneumonia, idiopathic pulmonary fibrosis, hypersensitive pneumonia, cancer (e.g., esophageal cancer, thyroid cancer, urinary bladder cancer, colorectal cancer, gastric cancer, pancreatic cancer, chest cancer, liver cancer, lung cancer, non-small cell lung cancer, breast cancer, neuroblastoma, glioblastoma, uterine cancer, cervical cancer, ovarian cancer, Wilms' tumor, prostate cancer, osteosarcoma), transplantation disease (e.g., graft rejections, graft-versus-host disease), allergy (e.g., allergic rhinitis, atopic dermatitis, food hypersensitivity, urticaria, hypersensitivity pneumonitis), ANCA associated disease, Duchenne muscular dystrophy, emphysema, pulmonary edema, pulmonary tuberculosis, pulmonary alveolar proteinosis, pulmonary lymphangioleiomyomatosis (LAM), pneumothorax, pleurisy, postoperative adhesion, endometriosis, adult periodontitis, bronchitis, chronic obstructive pulmonary diseases (COPD), infections, age-related macular degeneration, retinopathy, glaucoma, cataract, uveitis, Behcet's disease, hepatitis, cirrhosis, liver failure, renal infarct, nephritis, renal failure, cystitis, cerebral infarction, cerebral hemorrhage, intracranial hemorrhage, subarachnoid hemorrhage, hypertensive encephalopathy, cerebral embolism, transient cerebral ischemic attack, osteomyelitis, pyogenic arthritis, osteoporosis, hernia of intervertebral disk, gout and the like.

The aptamer or complex of the present invention can also be used as a drug delivery vehicle, a probe for in vivo imaging, a probe for determination of blood concentrations of IL-17, a probe for histological staining, a probe for ELISA, and a ligand for separation and purification of IL-17.

IL-17 is known to act on various cells such as fibroblasts, endothelial cells, epithelial cells, chondrocytes, osteoblasts, dendritic cell progenitors, marrow-derived interstitial cells, T cells, macrophages, and neutrophils. IL-17 induces the production and expression of various cytokines, chemokines, receptors, adhesion molecule, enzyme and the like by acting on these cells. Specifically, CXCL1 (KC or Groα), CXCL2 (MIP2 or Groβ), CXCL5 (LIX), CXCL6 (GCP-2), CXCL8 (IL-8), CXCL9 (MIG), CXCL10 (IP10), CXCL11 (I-TAC), CCL2 (MCP-1), CCL5 (RANTES), CCL7 (MCP-3), CCL11 (Eotaxin), CXCL12 (SDF-1), CCL20 (MIP3α), IL-1, IL-6, IL-19, TNF, CSF2 (GM-CSF), CSF3 (G-CSF), ICAM-1, VCAM-1, PTGS2 (COX2), NOS2 (iNOS), LCN2 (24p3), DEFB4 (BD2), S100A7 (Psoriasin), S100A8 (Calgranulin A), S100A9 (Calgranulin B), MUC5AC, MUC5B, EREG, SOCS3, TNFSF11 (RANKL), MMP1, MMP3, MMP9, MMP13, TIMP1, ADAMTS4, PGE2, SCF, CD80, CD86, MHC and the like can be mentioned. Therefore, the aptamer or complex of the present invention can be used as a medicament, diagnostic drug, examination drug, or reagent for diseases associated with these cells and cytokines, chemokines and the like.

By binding to an IL-17 receptor, IL-17 activates Act1 and TRAF6, and activates the NF-κB pathway, MAP kinase pathway, C/EBP pathway and the like. Therefore, the aptamer or complex of the present invention can be used as a medicament, diagnostic drug, examination drug, or reagent for diseases associated with the activation of these signal transduction pathways.

The aptamer of the present invention or complex can be used for the prophylaxis or treatment of inflammatory diseases and autoimmune diseases and the like (e.g., multiple sclerosis (MS), systemic lupus erythematosus (SLE), ankylosing spondylitis (AS), Sjögren's syndrome, polymyositis (PM), dermatomyositis (DM), rheumatoid arthritis (RA), osteoarthritis (OA), inflammatory bowel disease (Crohn's disease and the like), systemic sclerosis (PSS), scleroderma, periarteritis nodosa (PN), thyroid gland disease (Graves' disease, Hashimoto's thyroiditis, and the like), Guillain-Barre syndrome, primary biliary cirrhosis (PBC), idiopathic thrombocytopenic purpura, autoimmune hemolytic anemia, myasthenia gravis (MG), amyotrophic lateral sclerosis (ALS), Type I diabetes mellitus, plaque psoriasis, pustular psoriasis, asthma, neutrophil functional abnormalities, eosinophilic pneumonia, idiopathic pulmonary fibrosis, hypersensitive pneumonia), cancer (e.g., esophageal cancer, thyroid cancer, urinary bladder cancer, colorectal cancer, gastric cancer, pancreatic cancer, chest cancer, liver cancer, lung cancer, non-small cell lung cancer, breast cancer, neuroblastoma, glioblastoma, uterine cancer, cervical cancer, ovarian cancer, Wilms' tumor, prostate cancer, osteosarcoma), transplantation disease (e.g., rejection, graft-versus-host disease), allergy (e.g., allergic rhinitis, atopic dermatitis, food hypersensitivity, urticaria, hypersensitivity pneumonitis), ANCA associated disease, Duchenne muscular dystrophy, emphysema, lung edema, pulmonary tuberculosis, hypersensitivity pneumonitis, pulmonary proteinosis, pulmonary lymphangioleiomyomatosis (LAM), pneumothorax, pleurisy, postoperative adhesion, endometriosis, adult periodontitis, bronchitis, chronic obstructive pulmonary diseases (COPD), infections, age-related macular degeneration, retinopathy, glaucoma, cataract, uveitis, Behcet's disease, hepatitis, cirrhosis, liver failure, renal infarct, nephritis, renal failure, cystitis, cerebral infarction, cerebral hemorrhage, intracranial hemorrhage, subarachnoid hemorrhage, hypertensive encephalopathy, cerebral embolism, transient cerebral ischemic attack, osteomyelitis, pyogenic arthritis, osteoporosis, hernia of intervertebral disk, and gout.

The medicament of the present invention can be one formulated with a pharmaceutically acceptable carrier. Examples of the pharmaceutically acceptable carrier include, but are not limited to, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as citric acid, sodium citrate, and acetic acid; suspention such as methylcellulose, polyvinylpyrrolidone, and aluminum stearate; dispersant such as surfactants; diluents such as water, saline, and orange juice; base waxes such as cacao butter, polyethylene glycol, and white kerosene; and the like.

Preparations suitable for oral administration are a solution prepared by dissolving an effective amount of ligand in a diluent such as water, saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The medicament of the present invention can be coated by a method known per se for the purpose of taste masking, enteric dissolution, sustained release and the like. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), pigments (e.g., ferric oxide red, titanium dioxide and the like) and the like are used. The medicament may be a rapid-release preparation or sustained-release preparation. Examples of sustained-release bases include liposome, atelocollagen, gelatin, hydroxyapatite, PLGA and the like.

As preparations suitable for parenteral administration (e.g., intravenous administration, subcutaneous administration, intramuscular administration, topical administration, intraperitoneal administration, intranasal administration, pulmonary administration and the like), aqueous and non-aqueous isotonic sterile injectable liquids are available, which may comprise an antioxidant, a buffer solution, a bactericidal agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampule or a vial in a unit dosage volume or in several divided doses. An active ingredient and a pharmaceutically acceptable carrier can also be freeze-dried and stored in a state that may be dissolved or suspended in an appropriate sterile vehicle just before use. In addition to liquid injections, inhalants and ointments are also acceptable. In the case of an inhalant, an active ingredient in a freeze-dried state may be micronized and administered by inhalation using an appropriate inhalation device, inhalation using a nebulizer or the like. An inhalant can be mixed as appropriate with a conventionally used surfactant, oil, seasoning, cyclodextrin or derivative thereof and the like as required.

Here, examples of the surfactant include oleic acid, lecithin, diethylene glycol dioleate, tetrahydroflufuryl oleate, ethyl oleate, isopropyl myristate, glyceryl trioleate, glyceryl monolaurate, glyceryl monooleate, glyceryl monostearate, glyceryl monolysinoate, cetyl alcohol, stearyl alcohol, polyethyleneglycol 400, cetylpyridinium chloride, sorbitan trioleate (trade name, Span 85), sorbitan monooleate (trade name, Span 80), sorbitan monolaurate (trade name, Span 20), polyoxyethylene hardened castor oil (trade name, HCO-60), polyoxyethylene (20) sorbitan monolaurate (trade name, Tween 20), polyoxyethylene (20) sorbitan monooleate (trade name, Tween 80), lecithin of natural resource origin (trade name, EPICLON), oleylpolyoxyethylene (2) ether (trade name, Brij 92), stearyl polyoxyethylene (2) ether (trade name, Brij 72), lauryl polyoxyethylene (4) ether (trade name, Brij 30), oleylpolyoxyethylene (2) ether (trade name, Genapol 0-020), block copolymer of oxyethylene and oxypropylene (trade name, Synperonic) and the like. Examples of the oil include corn oil, olive oil, cottonseed oil, sunflower oil and the like. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an active ingredient, and used as a preparation.

An inhalant can be produced according to a conventional method. Specifically, an inhalant can be produced by powdering or liquefying the above-described aptamer or complex of the present invention, blending it in an inhalation propellant and/or carrier, and filling them in an appropriate inhalation vessel. When the above-described aptamer or complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as nitrogen gas and carbon dioxide gas and the like can be mentioned.

The dosage of the pharmaceutical of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The present invention also provides a solid phase carrier having the aptamer or the complex of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicon substrates, alumina substrates and the like, and substrates prepared by coating these substrates with a polymer and the like can be mentioned. As examples of the resin, agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of allyldextran and N,N'-methylenebisacrylamide, monodispersed synthetic polymers, monodispersed hydrophilic polymers, Sepharose, Toyopearl and the like can be mentioned, and also resins prepared by binding various functional groups to these resins were included. The solid phase carrier of the present invention can be useful in, for example, purifying, detecting and quantifying IL-17.

The aptamer or the complex of the present invention can be immobilized onto a solid phase carrier by a method known per se. For example, a method that introduces an affinity substance (e.g., those described above) or a predetermined functional group into the aptamer or the complex of the present invention, and then immobilizing the aptamer or complex onto a solid phase carrier via the affinity substance or predetermined functional group can be mentioned. The present invention also provides such methods. The predetermined functional group can be a functional group that can be subjected to a coupling reaction; for example, an amino group, a thiol group, a hydroxyl group, and a carboxyl group can be mentioned. The present invention also provides an aptamer having such a functional group introduced thereto.

The present invention also provides a method of purifying and concentrating IL-17. In particular, the present invention makes it possible to separate IL-17 from the proteins of other family proteins.

Therefore, in one embodiment, the present invention provides a purification method of IL-17, comprising (a) a step of contacting the aptamer or complex of the present invention with a sample containing IL-17 to allow binding of IL-17 in the sample to the aptamer or complex, and (b) a step of separating IL-17 bound to the aptamer or complex from the sample.

The method of purification and concentration of the present invention can comprise adsorbing IL-17 to the solid phase carrier of the present invention, and eluting the adsorbed IL-17 with an eluent. Adsorption of IL-17 to the solid phase carrier of the present invention can be achieved by a method known per se. For example, an IL-17-containing sample (e.g., bacterial or cell culture, culture supernatant, or blood) is introduced into the solid phase carrier of the present invention or a composition containing the same. IL-17 can be eluted using an eluent such as a neutral solution. There is no limitation on the neutral eluent, which can have a pH of, for example, about 6 to about 9, preferably about 6.5 to about 8.5, and more preferably about 7 to about 8. The neutral solution can also comprise, for example, a potassium salt (e.g., KCl), a sodium salt (e.g., NaCl), a magnesium salt (e.g., $MgCl_2$), a surfactant (e.g., Tween 20, Triton, NP40), and glycerin. The method of purification and concentration of the present invention can further comprise washing the solid phase carrier using a washing solution after IL-17 adsorption. Examples of the washing solution include those containing urea, a chelating agent (e.g., EDTA), Tris, an acid, an alkali, Transfer RNA, DNA, surfactants such as Tween 20, salts such as NaCl and the like. The method of purification and concentration of the present invention can still further comprise heating the solid phase carrier. This step enables the regeneration and sterilization of the solid phase carrier.

The aptamer or complex of the present invention can be utilized as a detection probe, particularly as a probe for detection of IL-17. The method of labeling the aptamer is not particularly limited; methods known per se can be applied. Such methods include, for example, labeling with a radioisotope, labeling with a fluorescent dye or fluorescent protein, and the like.

The present invention also provides a method of detecting and quantifying IL-17. In particular, the present invention makes it possible to detect and quantify IL-17 separately from the proteins of other family proteins. The method of detection and quantitation of the present invention can comprise measuring IL-17 by utilizing the aptamer of the present invention (e.g., by the use of the complex and solid phase carrier of the present invention).

Therefore, in one embodiment, the present invention provides a detection method of IL-17, comprising (a) a step of contacting the aptamer or complex of the present invention with a test sample to allow binding of IL-17 in the sample to the aptamer or complex, and (b) a step of detecting IL-17 bound to the aptamer or complex.

The method of detecting and quantifying IL-17 can be performed in the same manner as an immunological method, except that the aptamer of the present invention is used in place of an antibody. Therefore, by using the aptamer of the present invention in place of an antibody, in the same manner as such methods as enzyme immunoassay (EIA) (e.g., direct competitive ELISA, indirect competitive ELISA, sandwich ELISA), radioimmunoassay (RIA), fluorescent immunoassay (FIA), Western blotting (use in place of a secondary antibody in Western blot technique), immunohistochemical staining method, and cell sorting method, detection and quantitation can be performed. These methods can be useful not only in, for example, measuring IL-17 contents in living organisms or biological samples, and in diagnosing a disease associated with IL-17, but also for objects other than disease diagnosis such as scientific object, experiment and study object, and the like, including detection or quantification of IL-17 by using the aptamer of the present invention instead of an antibody, and a biological sample derived from human or animal other than human, or a sample other than biological samples.

The disclosures in all publications mentioned herein, including patents and patent application specifications, are incorporated by reference herein in the present invention to the extent that all of them have been given expressly.

The present invention is hereinafter described in more detail by means of the following Examples, which, however, never limit the scope of the invention.

EXAMPLES

Example 1-1: Preparation of Aptamer that Inhibits Binding of IL-17 and IL-17 Receptor—1

The aptamers represented by aptamer Nos. 1-49 described below were synthesized as follows according to the phosphoramidite method by using an automatic synthesizer. Using a solid phase synthesizer and nucleotide having the 3'-terminus carried by a resin as a starting material, the nucleotide was set on a synthesis column, and reaction solutions were passed through the synthesis column in the order of a deprotection solution, an activating solution and β-cyanoethylphosphoramidite of nucleotide adjacent to the 3'-terminus, oxidizing solution or sulfating reagent, and a capping solution of unreacted nucleotides to form a phosphodiester or phosphorothioate bond between nucleotides. In the same manner, one base was extended and synthesized each time in the 3'→5' direction. Thereafter, it was cleaved out from the solid phase carrier, and the protecting group of the base part and the protecting group of the phosphoric acid part were removed. Thereafter, a predetermined aptamer was obtained by cartlidge purification (see, for example, JP-A-2011-50381).

The nucleotide sequence of each of the obtained aptamers is shown below. Note that a, g, c, u are each an RNA wherein the base is adenine, guanine, cytosine and uracil, respectively, A, G, C, T are each a DNA wherein the base is adenine, guanine, cytosine and thymine, respectively, mc is an RNA wherein the base is methylcytosine. Parentheses in nucleotide indicate modification of the nucleotide, (M) indicates that, when the nucleotide is an RNA, a hydroxyl group at the 2'-position of ribose therein is substituted by an O-methyl group, and (F) indicates that, when the nucleotide is an RNA, a hydroxyl group at the 2'-position of ribose therein is substituted by a fluorine atom. (S) indicates that nucleotide is phosphorothioated, and (L) indicates modification with LNA. For example, c(F) is cytidine wherein a hydroxyl group at the 2'-position of ribose is substituted by a fluorine atom, a (M) is adenosine wherein the 2'-position of ribose is substituted by an O-methyl group, and g(M) is guanosine wherein the 2'-position of ribose is substituted by an O-methyl group (hereinafter to be described similarly).

Each sequence begins with the 5' end, and the terminal is the 3' end.

Aptamer No. 1
g(L)g(L)g(L)u(F)ag(S)c(F)c(F)g(S)gaggagu(F)c(F)agu(F)aau(F)c(F)ggu(F)amc(L)mc(L)mc(L) (SEQ ID NO: 1)

Aptamer No. 2:
g(M)g(M)g(M)u(F)ag(S)c(F)c(F)Gg(M)aggagu(F)c(F)agu(F)aau(F)c(F)ggu(F)aCCC (SEQ ID NO: 2)

Aptamer No. 3:
g(M)g(M)g(M)u(M)a(M)gc(M)c(M)Gg(M)a(F)gg(M)a(M)gu(F)c(F)a(F)gu(F)a(M)a(M)u(M)c(M)g(M)g(M)u(F)ACCC (SEQ ID NO: 3)

Aptamer No. 4:

g(M)g(M)g(M)u(M)Ag(S)c(M)c(M)Gg(M)a(F)gg(M)a(M)gu(F)c(F)a(F)gu(F)a(M)a(M)u(M)c(M)g(M)g(M)u(F)a(M)CCC (SEQ ID NO: 4)

Aptamer No. 5 g(M)g(M)g(M)g(M)u(M)a(M)g(S)c(M)c(M)Gg(M)a(F)gg(M)a(M)gTc(F)a(F)gTa(M)a(M)u(M)c(M)g(M)g(M)u(F)ACCCC (SEQ ID NO: 5)

Aptamer No. 6:

g(M)g(M)g(M)u(M)a(M)g(S)c(M)c(M)Gg(M)Agg(M)a(M)gTc(F)a(F)gTa(M)a(M)u(M)c(M)g(M)g(M)u(F)ACCC (SEQ ID NO: 6)

Aptamer No. 7:

g(M)g(M)g(M)u(M)Ag(S)c(M)c(M)Gg(M)a(F)gg(M)a(M)gu(F)c(F)a(F)gu(F)aau(M)c(M)g(M)g(M)u(F)a(M)CCC (SEQ ID NO: 7)

Aptamer No. 8:

g(M)g(M)g(M)u(M)Ag(S)c(M)c(M)Gg(M)a(F)gg(M)a(M)gTc(F)a(F)gTaau(M)c(M)g(M)g(M)u(F)a(M)CCC (SEQ ID NO: 8)

Aptamer No. 9:

g(M)g(M)g(M)u(M)Ag(S)c(M)c(M)Gg(M)a(F)gg(M)a(M)gTc(F)a(F)gTa(M)a(M)u(M)c(M)g(M)g(M)u(F)a(M)CCC (SEQ ID NO: 9)

Aptamer No. 10:

g(M)g(M)g(M)u(M)a(M)g(S)c(M)c(M)Gg(M)a(F)gg(M)a(M)gTc(F)a(F)gTa(M)Au(M)c(M)g(M)g(M)u(F)ACCC (SEQ ID NO: 10)

Aptamer No. 11:

g(M)g(M)g(M)u(M)Ag(S)c(M)c(M)Gg(M)a(F)gg(M)a(M)gTc(F)a(F)gTa(M)Au(M)c(M)g(M)g(M)u(F)a(M)CCC (SEQ ID NO: 11)

Aptamer No. 12:

g(M)g(M)g(M)u(M)Agc(M)c(M)Gg(M)a(F)gg(M)a(M)gTc(F)a(F)gTa(M)a(M)u(M)c(M)g(M)g(M)u(F)a(M)CCC (SEQ ID NO: 12)

Aptamer No. 13:

g(M)g(M)g(M)u(M)Agc(M)c(M)Gg(M)a(F)gg(M)a(M)gTc(F)a(F)gTa(M)Au(M)c(M)g(M)g(M)u(F)a(M)CCC (SEQ ID NO: 13)

Aptamer No. 14:

g(M)g(M)g(M)u(M)Ag(F)c(M)c(M)Gg(M)a(F)gg(M)a(M)gTc(F)a(F)gTa(M)a(M)u(M)c(M)g(M)g(M)u(F)a(M)CCC (SEQ ID NO: 14)

Aptamer No. 15:

g(M)g(M)g(M)u(M)Ag(F)c(M)c(M)Gg(M)a(F)gg(M)a(M)gTc(F)a(F)gTa(M)Au(M)c(M)g(M)g(M)u(F)a(M)CCC (SEQ ID NO: 15)

Aptamer No. 16:

g(M)g(M)g(M)g(M)u(M)Ag(S)c(M)c(M)Gg(M)a(F)gg(M)a(M)gTc(F)a(F)gTa(M)a(M)u(M)c(M)g(M)g(M)u(F)a(M)CCCC (SEQ ID NO: 16)

Aptamer No. 17:

g(M)g(M)g(M)g(M)u(M)Ag(S)c(M)c(M)Gg(M)a(F)gg(M)a(M)gTc(F)a(F)gTa(M)Au(M)c(M)g(M)g(M)u(F)a(M)CCCC (SEQ ID NO: 17)

Aptamer No. 18:

g(M)g(M)g(M)g(M)u(M)Ag(S)c(M)c(M)Gg(M)a(F)gg(M)a(M)gTc(F)a(F)gTaau(M)c(M)g(M)g(M)u(F)a(M)CCCC (SEQ ID NO: 18)

Aptamer No. 19:

g(M)g(M)g(M)u(M)Ag(S)c(M)c(M)Gg(M)Agg(M)a(M)gTc(F)a(F)gTa(M)a(M)u(M)c(M)g(M)g(M)u(F)a(M)CCC (SEQ ID NO: 19)

Aptamer No. 20:

g(M)g(M)g(M)u(M)Ag(S)c(M)c(M)Gg(M)Agg(M)a(M)gTc(F)a(F)gTa(M)Au(M)c(M)g(M)g(M)u(F)a(M)CCC (SEQ ID NO: 20)

Aptamer No. 21:

g(M)g(M)g(M)u(M)Ag(S)c(M)c(M)gg(M)Agg(M)a(M)gTc(F)agTaau(M)c(M)g(M)g(M)Ta(M)c(M)c(M)c(M) (SEQ ID NO: 21)

Aptamer No. 22:

g(M)g(M)g(M)u(M)Agc(M)c(M)gg(M)Agg(M)a(M)gTc(F)agTaau(M)c(M)g(M)g(M)Ta(M)c(M)c(M)c(M) (SEQ ID NO: 22)

Aptamer No. 23:

g(M)g(M)g(M)u(M)Ag(S)c(M)c(M)gg(M)Agg(M)a(M)gTc(F)agTaau(M)c(M)g(M)g(M)TAc(M)c(M)c(M) (SEQ ID NO: 23)

Aptamer No. 24:

g(M)g(M)g(M)u(M)Agc(M)c(M)gg(M)Agg(M)a(M)gTc(F)agTaau(M)c(M)g(M)g(M)TAc(M)c(M)c(M) (SEQ ID NO: 24)

Aptamer No. 25:

g(M)g(M)g(M)u(M)Agc(M)c(M)gg(M)Agg(M)a(M)gTc(F)agTa(M)Au(M)c(M)g(M)g(M)TAc(M)c(M)c(M) (SEQ ID NO: 25)

Aptamer No. 26:

g(M)g(M)g(M)u(M)Ag(S)c(M)c(M)Gg(M)Agg(M)a(M)gTc(F)agTaau(M)c(M)g(M)g(M)Ta(M)c(M)c(M)c(M) (SEQ ID NO: 26)

Aptamer No. 27:

g(M)g(M)g(M)u(M)Ag(S)c(M)c(M)Gg(M)Agg(M)a(M)gTc(F)agTa(M)Au(M)c(M)g(M)g(M)Ta(M)c(M)c(M)c(M) (SEQ ID NO: 27)

Aptamer No. 28:

g(M)g(M)g(M)u(M)Agc(M)c(M)Gg(M)Agg(M)a(M)gTc(F)agTaau(M)c(M)g(M)g(M)Ta(M)c(M)c(M)c(M) (SEQ ID NO: 28)

Aptamer No. 29:

g(M)g(M)g(M)u(M)Agc(M)c(M)Gg(M)Agg(M)a(M)gTc(F)agTa(M)a(M)u(M)c(M)g(M)g(M)Ta(M)c(M)c(M)c(M) (SEQ ID NO: 29)

Aptamer No. 30:

g(M)g(M)g(M)u(M)Agc(M)c(M)Gg(M)Agg(M)a(M)gTc(F)agTa(M)Au(M)c(M)g(M)g(M)Ta(M)c(M)c(M)c(M) (SEQ ID NO: 30)

Aptamer No. 31:

g(M)g(M)g(M)u(M)Ag(S)c(M)c(M)Gg(M)Agg(M)a(M)gTc(F)agTaau(M)c(M)g(M)g(M)TAc(M)c(M)c(M) (SEQ ID NO: 31)

Aptamer No. 32:

g(M)g(M)g(M)u(M)Agc(M)c(M)gg(M)Agg(M)a(M)gTc(F)agTa(M)a(M)u(M)c(M)g(M)g(M)TACCC (SEQ ID NO: 32)

Aptamer No. 33:

g(M)g(M)g(M)u(M)Agc(M)c(M)gg(M)Agg(M)a(M)gTc(F)agTa(M)Au(M)c(M)g(M)g(M)TACCC (SEQ ID NO: 33)

Aptamer No. 34:
g(M)g(M)g(M)u(M)Agc(M)c(M)Gg(M)Agg(M)a(M)gTc(F)AgTa(M)a(M)u(M)c(M)g(M)g(M)Ta(M)c(M)c(M)c(M) (SEQ ID NO: 34)

Aptamer No. 35:
g(M)g(M)g(M)u(M)Agc(M)c(M)Gg(M)Agg(M)a(M)gTc(F)AgTa(M)Au(M)c(M)g(M)g(M)Ta(M)c(M)c(M)c(M) (SEQ ID NO: 35)

Aptamer No. 36:
g(M)g(M)g(M)u(M)AGc(M)c(M)Gg(M)Agg(M)a(M)gTc(F)agTa(M)Au(M)c(M)g(M)g(M)Ta(M)c(M)c(M)c(M) (SEQ ID NO: 36)

Aptamer No. 37:
g(M)g(M)g(M)u(M)Agc(M)c(M)Gg(M)Agg(M)a(M)gTc(F)agTaAu(M)c(M)g(M)g(M)Ta(M)c(M)c(M)c(M) (SEQ ID NO: 37)

Aptamer No. 38:
g(M)g(M)g(M)u(M)Agc(M)c(M)Gg(M)Agg(M)a(M)gTc(F)agTa(M)au(M)c(M)g(M)g(M)Ta(M)c(M)c(M)c(M) (SEQ ID NO: 38)

Aptamer No. 39:
g(M)g(M)g(M)u(M)Agc(M)c(M)Gg(M)Agg(M)a(M)gTc(F)AgTaa(M)u(M)c(M)g(M)g(M)Ta(M)c(M)c(M)c(M) (SEQ ID NO: 39)

Aptamer No. 40:
g(M)g(M)g(M)u(M)Agc(M)c(M)Gg(M)Agg(M)a(M)gTc(F)AgTa(M)au(M)c(M)g(M)g(M)Ta(M)c(M)c(M)c(M) (SEQ ID NO: 40)

Aptamer No. 41:
g(M)g(M)g(M)u(M)Agc(M)c(M)Gg(M)agg(M)a(M)gTc(F)agTaau(M)c(M)g(M)g(M)Ta(M)c(M)c(M)c(M) (SEQ ID NO: 41)

Aptamer No. 42:
g(M)g(M)g(M)u(M)Agc(M)c(M)Gg(M)agg(M)a(M)gTc(F)agTaAu(M)c(M)g(M)g(M)Ta(M)c(M)c(M)c(M) (SEQ ID NO: 42)

Aptamer No. 43:
g(M)g(M)g(M)u(M)Agc(M)c(M)Gg(M)agg(M)a(M)gTc(F)agTa(M)au(M)c(M)g(M)g(M)Ta(M)c(M)c(M)c(M) (SEQ ID NO: 43)

Aptamer No. 44:
g(M)g(M)g(M)u(M)Agc(M)c(M)Gg(M)agg(M)a(M)gTc(F)AgTa(M)au(M)c(M)g(M)g(M)Ta(M)c(M)c(M)c(M) (SEQ ID NO: 44)

Aptamer No. 45:
g(M)g(M)g(M)u(M)Ag(S)c(M)c(M)Gg(M)agg(M)a(M)gTc(F)agTaau(M)c(M)g(M)g(M)u(F)a(M)CCC (SEQ ID NO: 45)

Aptamer No. 46:
g(M)g(M)g(M)u(M)Ag(S)c(M)c(M)Gg(M)Agg(M)a(M)gTc(F)agTaau(M)c(M)g(M)g(M)u(F)a(M)CCC (SEQ ID NO: 46)

Aptamer No. 47:
g(M)g(M)g(M)u(M)Agc(M)c(M)Gg(M)a(F)gg(M)a(M)gTc(F)a(F)gTaau(M)c(M)g(M)g(M)u(F)a(M)CCC (SEQ ID NO: 47)

Aptamer No. 48:
g(M)g(M)g(M)u(M)Agc(M)c(M)Gg(M)agg(M)a(M)gTc(F)agTaau(M)c(M)g(M)g(M)u(F)a(M)CCC (SEQ ID NO: 48)

Aptamer No. 49:
g(M)g(M)g(M)u(M)Agc(M)c(M)Gg(M)Agg(M)a(M)gTc(F)agTaau(M)c(M)g(M)g(M)u(F)a(M)CCC (SEQ ID NO: 49)

Whether aptamers shown by aptamer Nos. 1-49 inhibit the binding of IL-17 and IL-17 receptor was evaluated by the surface plasmon resonance method.

For the measurement, BIAcore2000 manufactured by BIAcore was used. Protein A (21181, PIERCE) was immobilized on a CM5 sensor chip, and recombinant human IL-17R-Fc chimera (177-IR, R&D systems) wherein Fc portion of IgG was fused was immobilized thereon at about 20 RU. As an analyte, IL-17 (100 or 150 nM) and an aptamer (50 or 100 nM) shown by aptamer No. 1-49 were mixed, maintained for 15 min and after that the mixture was flown.

The results of binding capacity of IL-17 and IL-17 receptor are shown in Table 2 below. In Table 2, an effect of the aptamer of the present invention on the binding capacity of IL-17 and IL-17 receptor is shown as a relative value to the binding amount of IL-17 and IL-17 receptor as 100. In addition, the IL-17 aptamer described in the prior art reference WO 2010/008001 was produced and used for comparison with the aptamer of the present invention. The sequence of the produced aptamer is as described below.

Aptamer No. 50
ggu(F)c(F)u(F)agc(F)c(F)ggaggagu(F)c(F)agu(F)aau(F)c(F)ggu(F)agac(F)c(F) (SEQ ID NO: 50)

The values shown in Table 2 indicate that the aptamer more strongly binds to IL-17 as the value becomes lower, that is, the aptamer has a high binding inhibitory activity against IL-17 and IL-17 receptor.

TABLE 2

Binding activity of IL-17 and IL-17 receptor

| | Binding capacity of IL-17 and IL-17 receptor (%) |
|---|---|
| IL-17 | 100 |
| aptamer No. 50 | 37.12 |
| aptamer No. 1 | 28.63 |
| aptamer No. 2 | 32.02 |
| aptamer No. 3 | 25.26 |
| aptamer No. 4 | 26.78 |
| aptamer No. 5 | 32.31 |
| aptamer No. 6 | 25.31 |
| aptamer No. 7 | 18.37 |
| aptamer No. 8 | 15.35 |
| aptamer No. 9 | 8.94 |
| aptamer No. 10 | 25.23 |
| aptamer No. 11 | 16.75 |
| aptamer No. 12 | 24.38 |
| aptamer No. 13 | 13.75 |
| aptamer No. 14 | 16.50 |
| aptamer No. 15 | 14.22 |
| aptamer No. 16 | 27.95 |
| aptamer No. 17 | 4.21 |
| aptamer No. 18 | 13.62 |
| aptamer No. 19 | 8.46 |
| aptamer No. 20 | 18.53 |
| aptamer No. 21 | 22.75 |
| aptamer No. 22 | 11.58 |
| aptamer No. 23 | 13.44 |
| aptamer No. 24 | 15.23 |
| aptamer No. 25 | 11.73 |
| aptamer No. 26 | 13.60 |
| aptamer No. 27 | 13.35 |
| aptamer No. 28 | 13.24 |
| aptamer No. 29 | 13.30 |
| aptamer No. 30 | 14.08 |
| aptamer No. 31 | 16.18 |
| aptamer No. 32 | 13.16 |
| aptamer No. 33 | 15.95 |
| aptamer No. 34 | 19.52 |
| aptamer No. 35 | 14.96 |
| aptamer No. 36 | 18.59 |
| aptamer No. 37 | 15.53 |
| aptamer No. 38 | 15.09 |
| aptamer No. 39 | 14.76 |
| aptamer No. 40 | 15.49 |
| aptamer No. 41 | 13.19 |
| aptamer No. 42 | 12.99 |
| aptamer No. 43 | 15.24 |

TABLE 2-continued

Binding activity of IL-17 and IL-17 receptor

| | Binding capacity of IL-17 and IL-17 receptor (%) |
|---|---|
| aptamer No. 44 | 17.88 |
| aptamer No. 45 | 19.21 |
| aptamer No. 46 | 20.03 |
| aptamer No. 47 | 17.65 |
| aptamer No. 48 | 19.24 |
| aptamer No. 49 | 19.04 |

As a result of the measurement, all the newly altered-modified aptamers showed an increased binding inhibitory activity as compared to the conventionally-known aptamer (aptamer No. 50). An aptamer having a high inhibitory activity showed about 8-fold higher binding inhibitory activity.

From the foregoing, it has been shown that the aptamer of the present invention has a high inhibitory activity against the binding of IL-17 and IL-17 receptor, as compared to conventionally-known aptamers.

Example 1-2: Preparation of Aptamer that Inhibits Binding of IL-17 and IL-17 Receptor—2

The aptamers represented by aptamer Nos. 52-94 described below were synthesized by the same method as in Example 1-1 and using an automatic synthesizer.

The nucleotide sequence of each of the obtained aptamers is shown below. Note that a, g, c, u are each an RNA wherein the base is adenine, guanine, cytosine and uracil, respectively, A, G, C, U, T are each a DNA wherein the base is adenine, guanine, cytosine, uracil and thymine, respectively, mc is an RNA wherein the base is methylcytosine. Parentheses in nucleotide indicate modification of the nucleotide, (M) indicates that, when the nucleotide is an RNA, a hydroxyl group at the 2'-position of ribose therein is substituted by an O-methyl group, and (F) indicates that, when the nucleotide is an RNA, a hydroxyl group at the 2'-position of ribose therein is substituted by a fluorine atom. (S) indicates that nucleotide is phosphorothioated, and (L) indicates modification with LNA. For example, c(F) is cytidine wherein a hydroxyl group at the 2'-position of ribose is substituted by a fluorine atom, a(M) is adenosine wherein the 2'-position of ribose is substituted by an O-methyl group, and g(M) is guanosine wherein the 2'-position of ribose is substituted by an O-methyl group (hereinafter to be described similarly).

Each sequence begins with the 5' end, and the terminal is the 3' end.

Aptamer No. 52:
g(M)g(M)g(M)u(M)Ag(S)c(M)c(M)Gg(M)a(F)gg(M)a(M)g(S)Tc(F)a(F)gTa(M)a(M)u(M)c(M)g(M)g(M)u(F)a(M)CCC (SEQ ID NO: 52)

Aptamer No. 53:
g(M)g(M)g(M)u(M)Ag(S)c(M)c(M)Gg(M)a(F)gg(M)a(M)gTc(F)a(F)g(S)Ta(M)a(M)u(M)c(M)g(M)g(M)u(F)a(M)CCC (SEQ ID NO: 53)

Aptamer No. 54:
g(M)g(M)g(M)u(M)Ag(S)c(M)c(M)Gg(M)a(F)gg(M)a(M)gUc(F)a(F)gUa(M)a(M)u(M)c(M)g(M)g(M)u(F)a(M)CCC (SEQ ID NO: 54)

Aptamer No. 55:
g(M)g(M)g(M)u(M)Ag(S)c(M)c(M)Gg(M)a(F)gg(M)a(M)gTc(F)a(F)gTgau(M)c(M)g(M)g(M)u(F)a(M)CCC (SEQ ID NO: 55)

Aptamer No. 56:
g(M)g(M)g(M)u(M)Ag(S)c(M)c(M)Gg(M)a(F)gg(M)a(M)g(S)Tc(F)a(F)g(S)Ta(M)a(M)u(M)c(M)g(M)g(M)u(F)a(M)CCC (SEQ ID NO: 56)

Aptamer No. 57:
g(M)g(M)g(M)u(M)Ag(S)c(M)c(M)Gg(M)a(F)gg(M)a(M)g(S)Tc(F)a(F)g(M)Ta(M)a(M)u(M)c(M)g(M)g(M)u(F)a(M)CCC (SEQ ID NO: 57)

Aptamer No. 58:
g(M)g(M)g(M)u(M)Ag(S)c(M)c(M)Gg(M)a(F)g(S)g(M)a(M)g(S)Tc(F)a(F)g(M)Ta(M)a(M)u(M)c(M)g(M)g(M)u(F)a(M)CCC (SEQ ID NO: 58)

Aptamer No. 59:
g(M)g(M)g(M)u(M)Ag(S)c(M)c(M)Gg(M)a(F)gg(M)a(M)g(S)Tc(F)a(F)g(M)Ta(M)a(M)u(M)c(M)g(M)g(M)u(F)a(M)c(M)c(M)c(M) (SEQ ID NO: 59)

Aptamer No. 60:
g(M)g(M)g(M)u(M)a(M)g(S)c(M)c(M)Gg(M)a(F)gg(M)a(M)g(S)Tc(F)a(F)g(M)Ta(M)a(M) u(M)c(M)g(M)g(M)u(F)a(M)c(M)c(M)c(M) (SEQ ID NO: 60)

Aptamer No. 61:
g(M)g(M)g(M)u(M)Ag(S)c(M)c(M)Gg(M)a(M)gg(M)a(M)g(S)Tc(F)a(F)g(M)Ta(M)a(M)u(M)c(M)g(M)g(M)u(F)a(M)CCC (SEQ ID NO: 61)

Aptamer No. 62:
g(M)g(M)g(M)u(M)a(M)g(S)c(M)c(M)Gg(M)a(F)gg(M)a(M)gTc(F)a(F)gTa(M)a(M)u(M)c(M)g(M)g(M)u(F)a(M)c(M)c(M)c(M) (SEQ ID NO: 62)

Aptamer No. 63:
g(M)g(M)g(M)u(M)a(M)g(S)c(M)c(M)Gg(M)a(F)gg(M)a(M)g(S)Tc(F)a(F)g(S)Ta(M)a(M)u (M)c(M)g(M)g(M)u(F)a(M)c(M)c(M)c(M) (SEQ ID NO: 63)

Aptamer No. 64:
g(M)g(M)g(M)u(M)a(M)g(S)c(M)c(M)Gg(M)a(F)gg(M)a(M)g(S)Tc(M)a(F)g(S)Ta(M)a(M) u(M)c(M)g(M)g(M)u(F)a(M)c(M)c(M)c(M) (SEQ ID NO: 64)

Aptamer No. 65:
g(M)g(M)g(M)u(M)a(M)g(S)c(M)c(M)Gg(M)a(F)gg(M)a(M)gTc(F)a(F)gTa(M)a(M)u(M)c(M)g(M)g(M)u(M)a(M)c(M)c(M)c(M) (SEQ ID NO: 65)

Aptamer No. 66:
g(M)g(M)g(M)u(M)a(M)g(S)c(M)c(M)Gg(M)a(F)gg(M)a(M)g(S)Tc(F)a(F)g(S)Ta(M)a(M)u (M)c(M)g(M)g(M)u(M)a(M)c(M)c(M)c(M) (SEQ ID NO: 66)

Aptamer No. 67:
g(M)g(M)g(M)u(M)a(M)g(S)c(M)c(M)Gg(M)a(F)gg(M)a(M)g(S)Tc(M)a(F)g(S)Ta(M)a(M) u(M)c(M)g(M)g(M)u(M)a(M)c(M)c(M)c(M) (SEQ ID NO: 67)

Aptamer No. 68:
g(M)g(M)g(M)u(M)a(M)g(S)c(M)c(M)Gg(M)a(F)gg(M)a(M)g(S)u(F)c(F)a(F)g(S)u(F)a(M)a (M)u(M)c(M)g(M)g(M)u(F)Ac(M)c(M)c(M) (SEQ ID NO: 68)

Aptamer No. 69:
g(M)g(M)g(M)u(M)a(M)g(S)c(M)c(M)Gg(M)a(F)gg(M)a(M)gu(F)c(F)a(F)gu(F)a(M)a(M)u(M)c(M)g(M)g(M)u(F)a(M)c(M)c(M)c(M) (SEQ ID NO: 69)

Aptamer No. 70:
g(M)g(M)g(M)u(M)a(M)g(S)c(M)c(M)Gg(M)a(F)gg(M)a(M)g(S)u(F)c(F)a(F)g(S)u(F)a(M)a (M)u(M)c(M)g(M)g(M)u(F)a(M)c(M)c(M)c(M) (SEQ ID NO: 70)

Aptamer No. 71:
g(M)g(M)g(M)u(M)a(M)g(S)c(M)c(M)Gg(M)a(F)gg(M)a(M)g(S)u(F)c(M)a(F)g(S)u(F)a(M) a(M)u(M)c(M)g(M)g(M)u(F)a(M)c(M)c(M)c(M) (SEQ ID NO: 71)

Aptamer No. 72:
g(M)g(M)g(M)u(M)a(M)g(S)c(M)c(M)Gg(M)a(F)gg(M)a(M)gu(F)c(F)a(F)gu(F)a(M)a(M)u(M)c(M)g(M)g(M)u(M)a(M)c(M)c(M)c(M) (SEQ ID NO: 72)

Aptamer No. 73:
g(M)g(M)g(M)u(M)a(M)g(S)c(M)c(M)Gg(M)a(F)gg(M)a(M)g(S)u(F)c(F)a(F)g(S)u(F)a(M)a (M)u(M)c(M)g(M)g(M)u(M)a(M)c(M)c(M)c(M) (SEQ ID NO: 73)

Aptamer No. 74:
g(M)g(M)g(M)u(M)a(M)gc(M)c(M)Gg(M)a(F)gg(M)a(M) gTc(F)a(F)gTa(M)a(M)u(M)c(M) g(M)g(M)u(F)a(M)c(M)c(M)c(M) (SEQ ID NO: 74)

Aptamer No. 75:
g(M)g(M)g(M)u(M)a(M)gc(M)c(M)gg(M)a(F)gg(M)a(M) gTc(F)a(F)gTa(M)a(M)u(M)c(M)g (M)g(M)u(F)a(M)c(M)c(M)c(M) (SEQ ID NO: 75)

Aptamer No. 76:
g(M)g(M)g(M)u(M)a(M)gc(M)c(M)Gg(M)a(F)gg(M)a(M) gu(F)c(F)a(F)gu(F)a(M)a(M)u(M) c(M)g(M)g(M)u(F)Ac(M)c(M)c(M) (SEQ ID NO: 76)

Aptamer No. 77:
g(M)g(M)g(M)u(M)a(M)gc(M)c(M)gg(M)a(F)gg(M)a(M) gu(F)c(F)a(F)gu(F)a(M)a(M)u(M) c(M)g(M)g(M)u(F)Ac(M)c(M)c(M) (SEQ ID NO: 77)

Aptamer No. 78:
g(M)g(M)g(M)u(M)a(M)gc(M)c(M)Gg(M)a(F)gg(M)a(M) gTc(F)a(F)gTa(M)a(M)u(M)c(M) g(M)g(M)u(M)a(M)c(M)c(M)c(M) (SEQ ID NO: 78)

Aptamer No. 79:
g(M)g(M)g(M)u(M)a(M)gc(M)c(M)gg(M)a(F)gg(M)a(M) gu(F)c(F)a(F)gu(F)a(M)a(M)u(M) c(M)g(M)g(M)u(M)a(M)c(M)c(M)c(M) (SEQ ID NO: 79)

Aptamer No. 80:
g(M)g(M)g(M)u(M)a(M)g(S)c(M)c(M)Gg(M)a(F)gg(M)a(M)gu(F)c(F)a(F)gu(F)a(M)a(M)u(M)c(M)g(M)g(M)u(F)Ac(M)c(M)c(M) (SEQ ID NO: 80)

Aptamer No. 81:
g(M)g(M)g(M)u(M)a(M)g(S)c(M)c(M)Gg(M)a(M)gg(M)a(M)g(S)Tc(M)a(F)g(S)Ta(M)a(M) u(M)c(M)g(M)g(M)u(M)a(M)c(M)c(M)c(M) (SEQ ID NO: 81)

Aptamer No. 82:
g(M)g(M)g(M)u(M)a(M)g(S)c(M)c(M)Gg(M)a(M)gg(M)a(M)g(S)Tc(F)a(F)g(S)Ta(M)a(M) u(M)c(M)g(M)g(M)u(M)a(M)c(M)c(M)c(M) (SEQ ID NO: 82)

Aptamer No. 83:
g(M)g(M)g(M)u(M)a(M)g(S)c(M)c(M)Gg(M)a(M)gg(M)a(M)g(S)u(F)c(M)a(F)g(S)u(F)a(M) a(M)u(M)c(M)g(M)g(M)u(F)a(M)c(M)c(M)c(M) (SEQ ID NO: 83)

Aptamer No. 84:
g(M)g(M)g(M)u(M)a(M)g(S)c(M)c(M)Gg(M)a(M)gg(M)a(M)g(S)u(F)c(F)a(F)g(S)u(F)a(M) a(M)u(M)c(M)g(M)g(M)u(M)a(M)c(M)c(M)c(M) (SEQ ID NO: 84)

Aptamer No. 85:
g(M)g(M)g(M)u(M)a(M)g(S)c(M)c(M)Gg(M)a(M)gg(M)a(M)g(S)u(F)c(F)a(F)g(S)u(F)a(M) a(M)u(M)c(M)g(M)g(M)u(F)a(M)c(M)c(M)c(M) (SEQ ID NO: 85)

Aptamer No. 86:
g(M)g(M)g(M)u(M)a(M)g(S)c(M)c(M)Gg(M)a(M)gg(M)a(M)g(S)Tc(M)a(F)g(S)Tg(M)a(M) u(M)c(M)g(M)g(M)u(M)a(M)c(M)c(M)c(M) (SEQ ID NO: 86)

Aptamer No. 87:
g(M)g(M)g(M)u(M)a(M)g(S)c(M)c(M)Gg(M)a(M)gg(M)a(M)g(S)Tc(M)a(F)g(S)Tga(M)u(M)c(M)g(M)g(M)u(M)a(M)c(M)c(M)c(M) (SEQ ID NO: 87)

Aptamer No. 88:
g(M)g(M)g(M)u(M)a(M)g(S)c(M)c(M)Gg(M)a(M)gg(M)a(M)g(S)u(F)c(M)a(F)g(S)u(F)ga(M)u(M)c(M)g(M)g(M)u(F)a(M)c(M)c(M)c(M) (SEQ ID NO: 88)

Aptamer No. 89:
g(M)g(M)g(M)u(M)a(M)g(S)c(M)c(M)Gg(M)a(M)gg(M)a(M)g(S)Tc(M)a(F)g(S)Taa(M)u(M)c(M)g(M)g(M)u(M)a(M)c(M)c(M)c(M) (SEQ ID NO: 89)

Aptamer No. 90:
g(M)g(M)g(M)u(M)a(M)g(S)c(M)c(M)Gg(M)a(M)gg(M)a(M)g(S)Tc(M)a(F)g(S)Ta(M)au(M)c(M)g(M)g(M)u(M)a(M)c(M)c(M)c(M) (SEQ ID NO: 90)

Aptamer No. 91:
g(M)g(M)g(M)u(M)a(M)g(S)c(M)c(M)Gg(M)a(M)gg(M)a(M)g(S)Tc(M)a(F)g(S)Taau(M)c(M)g(M)g(M)u(M)a(M)c(M)c(M)c(M) (SEQ ID NO: 91)

Aptamer No. 92:
g(M)g(M)g(M)u(M)a(M)g(S)c(M)c(M)Gg(M)a(M)gg(M)a(M)g(S)u(F)c(F)a(F)g(S)u(F)aa(M) u(M)c(M)g(M)g(M)u(F)a(M)c(M)c(M)c(M) (SEQ ID NO: 92)

Aptamer No. 93:
g(M)g(M)g(M)u(M)a(M)g(S)c(M)c(M)Gg(M)a(M)gg(M)a(M)g(S)u(F)c(F)a(F)g(S)u(F)a(M) au(M)c(M)g(M)g(M)u(F)a(M)c(M)c(M)c(M) (SEQ ID NO: 93)

Aptamer No. 94:
g(M)g(M)g(M)u(M)a(M)g(S)c(M)c(M)Gg(M)a(M)gg(M)a(M)g(S)u(F)c(F)a(F)g(S)u(F)aau(M)c(M)g(M)g(M)u(F)a(M)c(M)c(M)c(M) (SEQ ID NO: 94)

Whether the synthesized aptamers inhibit the binding of IL-17 and IL-17 receptor was evaluated by the surface plasmon resonance method.

For the measurement, BIAcore T100 manufactured by GE Healthcare Bio Sciences was used. Protein A (21181, PIERCE) was immobilized on a CM5 sensor chip, and recombinant human IL-17R-Fc chimera (177-IR, R&D systems) wherein Fc portion of IgG was fused was immobilized thereon at about 750 RU. As an analyte, IL-17 (150 nM) and each aptamer (12.5 or 50 nM) shown by Table 3 were mixed, maintained for 15 min and after that the mixture was flown.

The results of binding capacity of IL-17 and IL-17 receptor are shown in Table 3 below. In Table 3, an effect of the aptamer of the present invention on the binding capacity of IL-17 and IL-17 receptor is shown as a relative value to the binding amount of IL-17 and IL-17 receptor as 100. For comparison with the aptamer of the present invention, a conventionally-known aptamer (aptamer No. 50) against IL-17 was used.

The values shown in Table 3 indicate that the aptamer more strongly binds to IL-17 as the value becomes lower, that is, the aptamer has a high binding inhibitory activity against IL-17 and IL-17 receptor.

TABLE 3

| Binding activity of IL-17 and IL-17 receptor | |
|---|---|
| | Binding capacity of IL-17 and IL-17 receptor (%) |
| IL-17 | 100 |
| aptamer No. 50 | 37.12 |
| aptamer No. 52 | 27.55 |
| aptamer No. 53 | 22.65 |
| aptamer No. 54 | 25.15 |
| aptamer No. 55 | 18.99 |
| aptamer No. 56 | 26.96 |
| aptamer No. 58 | 33.72 |
| aptamer No. 59 | 36.54 |
| aptamer No. 60 | 31.88 |
| aptamer No. 62 | 25.92 |
| aptamer No. 63 | 27.10 |

TABLE 3-continued

Binding activity of IL-17 and IL-17 receptor

| | Binding capacity of IL-17 and IL-17 receptor (%) |
|---|---|
| aptamer No. 64 | 29.32 |
| aptamer No. 65 | 20.29 |
| aptamer No. 66 | 28.71 |
| aptamer No. 68 | 37.00 |
| aptamer No. 69 | 18.44 |
| aptamer No. 70 | 34.97 |
| aptamer No. 72 | 26.12 |
| aptamer No. 73 | 31.96 |
| aptamer No. 75 | 21.57 |
| aptamer No. 76 | 24.12 |
| aptamer No. 77 | 23.95 |
| aptamer No. 78 | 23.28 |
| aptamer No. 79 | 28.23 |
| aptamer No. 80 | 25.26 |
| aptamer No. 81 | 34.26 |
| aptamer No. 82 | 5.28 |
| aptamer No. 83 | 33.53 |
| aptamer No. 84 | 27.74 |
| aptamer No. 85 | 27.80 |
| aptamer No. 86 | 35.71 |
| aptamer No. 87 | 32.40 |
| aptamer No. 89 | 35.10 |
| aptamer No. 90 | 41.23 |
| aptamer No. 91 | 35.10 |
| aptamer No. 92 | 31.63 |
| aptamer No. 93 | 30.62 |
| aptamer No. 94 | 29.32 |

As a result of the measurement, all the newly altered-modified aptamers showed an increased binding inhibitory activity as compared to the conventionally-known aptamer (aptamer No. 50). The aptamer having a high inhibitory activity showed about 7-fold higher binding inhibitory activity.

From the foregoing, it has been shown that the aptamer of the present invention has a high inhibitory activity against the binding of IL-17 and IL-17 receptor, as compared to conventionally-known aptamers.

Example 2-1: Inhibitory Action of the Aptamer of the Present Invention Using Mouse Fibroblast NIH3T3 Cell Line—1

Mouse fibroblast NIH3T3 cell line extracellularly releases IL-6 by cell stimulation with IL-17 and TNFα. Utilizing this property, an aptamer having an IL-17 inhibitory action was selected.

First, human IL-17 and the aptamer produced in Example 1-1 were pre-incubated at 37° C. for 30 min, and added to NIH3T3 cell (ATCC, CRL1658) together with mouse TNFα (2 ng/mL). Then, after incubation for 24 hr, the culture supernatant was collected, and the amount of IL-6 was measured by BD Cytometric Bead Array (BD Biosciences). The IL-17 inhibitory action of each aptamer was determined from the amount of IL-6. The 50% inhibitory concentration ($IC_{50}$ value) is shown in the following Tables 4 and 5. For comparison with the aptamer of the present invention, a conventionally-known aptamer (aptamer No. 50) against IL-17 was used.

TABLE 4

IL-17 inhibitory action of various aptamers in mouse NIH3T3 cell line

| | $IC_{50}$ (nM) |
|---|---|
| aptamer No. 50 | 7.36 |
| aptamer No. 1 | 1.17 |
| aptamer No. 2 | 0.68 |
| aptamer No. 3 | 2.08 |
| aptamer No. 4 | 2.78 |
| aptamer No. 5 | 0.13 |
| aptamer No. 6 | 0.77 |
| aptamer No. 7 | 0.30 |
| aptamer No. 8 | 0.49 |
| aptamer No. 9 | 0.64 |
| aptamer No. 10 | 0.63 |
| aptamer No. 11 | 0.34 |
| aptamer No. 12 | 0.52 |
| aptamer No. 13 | 0.40 |
| aptamer No. 14 | 0.50 |
| aptamer No. 15 | 0.63 |
| aptamer No. 16 | 0.25 |
| aptamer No. 17 | 0.30 |
| aptamer No. 18 | 0.15 |
| aptamer No. 19 | 2.78 |
| aptamer No. 20 | 0.37 |
| aptamer No. 21 | 0.39 |
| aptamer No. 22 | 1.66 |
| aptamer No. 23 | 1.34 |
| aptamer No. 24 | 1.77 |
| aptamer No. 25 | 1.64 |

TABLE 5

IL-17 inhibitory action of various aptamers in mouse NIH3T3 cell line (continued)

| | $IC_{50}$ (nM) |
|---|---|
| aptamer No. 26 | 0.78 |
| aptamer No. 27 | 2.45 |
| aptamer No. 28 | 2.11 |
| aptamer No. 29 | 2.53 |
| aptamer No. 30 | 1.49 |
| aptamer No. 31 | 0.30 |
| aptamer No. 32 | 4.62 |
| aptamer No. 33 | 4.31 |
| aptamer No. 34 | 2.41 |
| aptamer No. 35 | 2.47 |
| aptamer No. 37 | 1.64 |
| aptamer No. 38 | 0.31 |
| aptamer No. 39 | 3.91 |
| aptamer No. 40 | 3.75 |
| aptamer No. 41 | 0.40 |
| aptamer No. 42 | 0.51 |
| aptamer No. 43 | 0.49 |
| aptamer No. 44 | 1.83 |
| aptamer No. 45 | 0.76 |
| aptamer No. 46 | 1.13 |
| aptamer No. 47 | 0.59 |
| aptamer No. 48 | 0.30 |
| aptamer No. 49 | 0.65 |

As a result of the measurement, the newly altered-modified aptamers showed an increased activity about 2-fold to 50-fold as compared to the conventionally-known aptamer (aptamer No. 50).

From the foregoing, it has been shown that the aptamer of the present invention inhibits physiological activity of IL-17 extremely strongly as compared to conventionally-known aptamers.

Example 2-2: Inhibitory Action of the Aptamer of the Present Invention Using Mouse Fibroblast NIH3T3 Cell Line—2

First, human IL-17 and the aptamer produced in Example 1-2 were pre-incubated at 37° C. for 30 min, and added to NIH3T3 cell (ATCC, CRL1658) together with mouse TNFα (2 ng/mL). Then, after incubation for 24 hr, the culture supernatant was collected, and the production amount of IL-6 was measured by ELISA method described below. The IL-17 inhibitory action of each aptamer was determined from the production amount of IL-6. The 50% inhibitory concentration (ICH value) is shown in the following Table 6. For comparison with the aptamer of the present invention, a conventionally-known aptamer (aptamer No. 50) against IL-17 was used.

ELISA method for verifying IL-17 inhibitory action of aptamer: A microtiter plate for ELISA was coated with rat anti-mouse IL-6 antibody (BD Biosciences, 2 μg/mL; 100 μL/well) diluted with PBS, and incubated at 4° C. overnight. The next day, the microtiter plate was washed 3 times with PBS/0.05% Tween 20, and applied blocking with PBS/1% BSA (200 μL/well) at room temperature for 2 hr. Then, the plate was washed 3 times with PBS/0.05% Tween 20. Recombinant mouse IL-6 (BD Biosciences; 100 μL/well) serially diluted with PBS/1% BSA/0.05% Tween 20 or culture supernatants (100 μL/well) were added to the plate. After incubation at room temperature for 2 hr, the plate was washed 3 times with PBS/0.05% Tween 20. Then, 100 μL/well of biotin conjugated rat anti-mouse IL-6 antibody (BD Biosciences) was added to the plate at final dilution of 1/500, and the mixture was reacted at room temperature for 1 hr. After washing 3 times with PBS/0.05% Tween 20, 100 μL/well of alkaline phosphatase conjugated streptavidin was added at final dilution of 1/1000. After 30 min at room temperature, the plate was again washed 4 times with PBS/0.05% Tween 20, and a substrate (1-Step PNPP; Thermo Fisher Scientific Inc; 100 μL/well) was added. After 15 min, aqueous sodium hydroxide solution (2N: 50 μL/well) was added to stop the reaction, and the plate was read on a microtiter reader (Bio-Rad) by using a 405 nm filter.

TABLE 6

IL-17 inhibitory action of various aptamers in mouse NIH3T3 cell line

|  | $IC_{50}$ (nM) |
| --- | --- |
| aptamer No. 50 | 8.63 |
| aptamer No. 52 | 1.11 |
| aptamer No. 53 | 1.67 |
| aptamer No. 55 | 0.11 |
| aptamer No. 56 | 0.52 |
| aptamer No. 57 | 2.36 |
| aptamer No. 59 | 1.19 |
| aptamer No. 60 | 2.35 |
| aptamer No. 61 | 3.41 |
| aptamer No. 62 | 0.69 |
| aptamer No. 63 | 0.81 |
| aptamer No. 64 | 4.64 |
| aptamer No. 65 | 0.67 |
| aptamer No. 66 | 1.21 |
| aptamer No. 67 | 5.95 |
| aptamer No. 68 | 2.40 |
| aptamer No. 69 | 1.73 |
| aptamer No. 70 | 3.28 |
| aptamer No. 71 | 5.54 |
| aptamer No. 72 | 2.24 |
| aptamer No. 73 | 3.46 |
| aptamer No. 74 | 1.06 |

TABLE 6-continued

IL-17 inhibitory action of various aptamers in mouse NIH3T3 cell line

|  | $IC_{50}$ (nM) |
| --- | --- |
| aptamer No. 75 | 1.33 |
| aptamer No. 76 | 1.70 |
| aptamer No. 77 | 4.66 |
| aptamer No. 78 | 1.36 |
| aptamer No. 79 | 2.25 |
| aptamer No. 80 | 1.52 |
| aptamer No. 81 | 2.26 |
| aptamer No. 82 | 0.48 |
| aptamer No. 84 | 1.04 |
| aptamer No. 85 | 0.96 |
| aptamer No. 86 | 5.16 |
| aptamer No. 87 | 3.23 |
| aptamer No. 88 | 2.88 |
| aptamer No. 89 | 6.21 |
| aptamer No. 90 | 1.08 |
| aptamer No. 91 | 3.86 |
| aptamer No. 92 | 2.60 |
| aptamer No. 93 | 0.22 |
| aptamer No. 94 | 0.29 |

As a result of the measurement, all the newly altered-modified aptamers showed an increased activity as compared to the conventionally-known aptamer (aptamer No. 50). An aptamer having a high inhibitory activity showed about 80-fold higher activity.

From the foregoing, it has been shown that the aptamer of the present invention inhibits physiological activity of IL-17 extremely strongly as compared to conventionally-known aptamers.

Example 3: IL-17 Inhibitory Action of the Aptamer of the Present Invention Against Connective Tissue-Derived Cell Normal human dermal fibroblast (NHDF) extracellularly releases IL-6 by cell stimulation with IL-17. Therefore, using NHDF as an example of a connective tissue-derived cell, the IL-17 inhibitory action of each aptamer was determined according to the method described in Arthritis Rheum. 63, 455-466 (2011).

First, NHDF (Lonza Japan Ltd.) was seeded in a 48 well microplate and incubated for 24 hr. Then, human IL-17 (1 or 2 ng/mL) and an pegylated aptamer (5 or 10 ng/mL) modified by the method described in the below-mentioned Example 5 were preincubated at 37° C. for 60 min, and added to NHDF. After further incubation for 24 hr, the culture supernatant was collected, and the IL-6 production amount was measured by the enzyme immunoassay (ELISA) method (Endogen Human IL-6 ELISA Kit: Thermo scientific). IL-17 inhibitory capacity is calculated from the amount of IL-6 production, and results are shown in Table 7 as a relative ratio to IL-17 inhibitory capacity of the conventionally-known aptamer (aptamer No. 50) against IL-17 as 1.

TABLE 7

IL-17 inhibitory action of various aptamers in normal human skin fibroblast

|  | IL-17 inhibitory capacity |
| --- | --- |
| aptamer No. 50 | 1.00 |
| aptamer No. 1 | 1.19 |
| aptamer No. 3 | 1.13 |
| aptamer No. 4 | 1.21 |

TABLE 7-continued

IL-17 inhibitory action of various aptamers in normal human skin fibroblast

| | IL-17 inhibitory capacity |
|---|---|
| aptamer No. 5 | 1.17 |
| aptamer No. 7 | 1.37 |
| aptamer No. 8 | 1.38 |
| aptamer No. 9 | 1.33 |
| aptamer No. 10 | 1.30 |
| aptamer No. 11 | 1.37 |
| aptamer No. 12 | 1.36 |
| aptamer No. 13 | 1.32 |
| aptamer No. 14 | 1.12 |
| aptamer No. 16 | 1.32 |
| aptamer No. 17 | 1.34 |
| aptamer No. 18 | 1.34 |
| aptamer No. 19 | 1.28 |
| aptamer No. 20 | 1.33 |
| aptamer No. 21 | 1.73 |
| aptamer No. 22 | 1.66 |
| aptamer No. 23 | 1.82 |
| aptamer No. 24 | 1.70 |
| aptamer No. 25 | 1.62 |
| aptamer No. 26 | 1.67 |
| aptamer No. 27 | 1.78 |
| aptamer No. 28 | 1.78 |
| aptamer No. 29 | 1.39 |
| aptamer No. 30 | 1.46 |
| aptamer No. 31 | 1.80 |
| aptamer No. 32 | 1.25 |
| aptamer No. 33 | 1.30 |
| aptamer No. 34 | 1.14 |
| aptamer No. 37 | 1.87 |
| aptamer No. 38 | 1.84 |
| aptamer No. 39 | 1.29 |
| aptamer No. 40 | 1.34 |
| aptamer No. 41 | 1.53 |
| aptamer No. 42 | 1.57 |
| aptamer No. 43 | 1.40 |
| aptamer No. 45 | 1.79 |
| aptamer No. 46 | 1.88 |
| aptamer No. 47 | 1.91 |
| aptamer No. 48 | 1.78 |
| aptamer No. 49 | 1.72 |

As a result of the measurement, the newly altered-modified aptamers showed an increased IL-17 inhibitory capacity as compared to the conventionally-known aptamer (aptamer No. 50).

From the foregoing, it has been shown that the aptamer of the present invention inhibits physiological activity of IL-17 extremely strongly against connective tissue-derived cell as compared to conventionally-known aptamers.

Example 4: IL-17 Inhibitory Action of the Aptamer of the Present Invention on Epithelial Tissue-Derived Cell Normal human epidermal keratinocyte (NHEK) extracellularly releases IL-6, IL-8, and CCL20 by cell stimulation with IL-17 and TNFα, and normal human renal proximal tubular epithelial cell (HRPTEC) releases IL-6, IL-8, and MCP-1 by cell stimulation with IL-17. Therefore, using NHEK and HRPTEC as examples of epithelial tissue, the IL-17 inhibitory action of the aptamer of the present invention was determined.

First, NHEK (KURABO INDUSTRIES LTD.) or HRPTEC (KURABO INDUSTRIES LTD.) was seeded in a 96 well microplate, and incubated for 24 hr. Then, human IL-17 (100 ng/mL) and the aptamer produced in Example 1-1 were preincubated at 37° C. for 30 min, and added to NHEK together with human TNFα (10 ng/mL). Similarly, human IL-17 (100 ng/mL) and the aptamer produced in Example 1-1 were preincubated at 37° C. for 30 min and added to HRPTEC. After incubation for 24 hr and 48 hr, the culture supernatant was collected, and CCL20, IL-6, IL-8, and MCP-1 were measured by ELISA (Quantikine Human CCL20/MIP-3 ELISA, R&D systems) or BD Cytmetric Bead Array.

The IL-17 inhibitory action of various aptamers on NHEK is shown below. For comparison with the aptamer of the present invention, a conventionally-known aptamer (aptamer No. 50) against IL-17 was used.

TABLE 8

IL-6 production inhibition ratio

| | IL-6 production inhibition ratio (%) | |
|---|---|---|
| aptamer amount added | 300 nM | 30 nM |
| aptamer No. 50 | 13.9 | 0.0 |
| aptamer No. 8 | — | 24.9 |
| aptamer No. 28 | — | 14.4 |
| aptamer No. 41 | — | 29.8 |
| aptamer No. 45 | — | 24.1 |
| aptamer No. 47 | — | 20.0 |
| aptamer No. 48 | — | 33.4 |

—: not performed

TABLE 9

IL-8 production inhibition ratio

| | IL-8 production inhibition ratio (%) | |
|---|---|---|
| aptamer amount added | 300 nM | 30 nM |
| aptamer No. 50 | 45.6 | 0.0 |
| aptamer No. 8 | — | 58.0 |
| aptamer No. 28 | — | 22.3 |
| aptamer No. 37 | — | 18.9 |
| aptamer No. 38 | — | 25.8 |
| aptamer No. 41 | — | 47.2 |
| aptamer No. 45 | — | 55.0 |
| aptamer No. 47 | — | 50.8 |
| aptamer No. 48 | — | 49.5 |

—: not performed

TABLE 10

CCL20 production inhibition ratio

| | CCL20 production inhibition ratio (%) | |
|---|---|---|
| aptamer amount added | 300 nM | 30 nM |
| aptamer No. 50 | 1.0 | 0.0 |
| aptamer No. 8 | — | 35.2 |
| aptamer No. 28 | — | 28.7 |
| aptamer No. 37 | — | 12.1 |
| aptamer No. 38 | — | 12.4 |
| aptamer No. 41 | — | 79.4 |
| aptamer No. 45 | — | 28.9 |
| aptamer No. 47 | — | 34.1 |
| aptamer No. 48 | — | 71.2 |

—: not performed

The IL-17 inhibitory action of various aptamers on HRPTEC is shown below. For comparison with the aptamer of the present invention, a conventionally-known aptamer (aptamer No. 50) against IL-17 was used.

TABLE 11

IL-6 production inhibition ratio

| | IL-6 production inhibition ratio (%) | |
|---|---|---|
| aptamer amount added | 300 nM | 30 nM |
| aptamer No. 50 | 47.4 | 17.5 |
| aptamer No. 8 | — | 53.5 |
| aptamer No. 25 | — | 33.1 |
| aptamer No. 28 | — | 42.8 |
| aptamer No. 37 | — | 30.7 |
| aptamer No. 38 | — | 42.7 |
| aptamer No. 41 | — | 58.9 |
| aptamer No. 45 | — | 48.2 |
| aptamer No. 47 | — | 47.1 |
| aptamer No. 48 | — | 53.8 |

—: not performed

TABLE 12

IL-8 production inhibition ratio

| | IL-8 production inhibition ratio (%) | |
|---|---|---|
| aptamer amount added | 300 nM | 30 nM |
| aptamer No. 50 | 63.6 | 40.3 |
| aptamer No. 8 | — | 73.1 |
| aptamer No. 25 | — | 56.5 |
| aptamer No. 28 | — | 60.8 |
| aptamer No. 37 | — | 55.4 |
| aptamer No. 38 | — | 64.3 |
| aptamer No. 41 | — | 79.7 |
| aptamer No. 45 | — | 70.6 |
| aptamer No. 47 | — | 71.7 |
| aptamer No. 48 | — | 72.7 |

—: not performed

TABLE 13

MCP1 production inhibition ratio

| | MCP1 production inhibition ratio (%) | |
|---|---|---|
| aptamer amount added | 300 nM | 30 nM |
| aptamer No. 50 | 67.9 | 36.5 |
| aptamer No. 8 | — | 69.6 |
| aptamer No. 25 | — | 53.2 |
| aptamer No. 28 | — | 62.7 |
| aptamer No. 37 | — | 56.9 |
| aptamer No. 38 | — | 64.8 |
| aptamer No. 41 | — | 74.1 |
| aptamer No. 45 | — | 63.8 |
| aptamer No. 47 | — | 69.8 |
| aptamer No. 48 | — | 70.6 |

—: not performed

As a result of the measurement, the newly altered-modified aptamers more strongly suppressed production of cytokines (IL-6, IL-8) and chemokines (CCL20, MCP1) induced by IL-17, than the conventionally-known aptamer (aptamer No. 50).

From the foregoing, it has been shown that the aptamer of the present invention inhibits physiological activity of IL-17 extremely strongly against epithelial tissue cell as compared to conventionally-known aptamers.

Example 5: Serum Stability Test I

The stability of each aptamer in human serum was evaluated in vitro.

Altered-modified aptamers were produced by adding PEG having a molecular weight of 40 or 80 kDa (SUNBRIGHT GL2-400GS2 manufactured by NOF Corporation, SUNBRIGHT GL2-400TS manufactured by NOF Corporation, SUNBRIGHT GL2-800GS2 manufactured by NOF Corporation, SUNBRIGHT GL4-800GS2 manufactured by NOF Corporation or Y-NHS-40K: Y-shape manufactured by Jenkem) to the 5'-terminus of the aptamer produced in Example 1-1 via a linker (ssH amino linker or C6 amino linker), and adding idT (inverted dT) to the 3'-terminus (refer to, for example, JP-B-3626503 for the production method).

The aptamer produced in Example 1-1 or the above-mentioned pegylated aptamer (100 μM 2 μL) was added to human serum (36 μL), and the mixture was stood at 37° C. After lapse of 0 hr, 24 hr, 48 hr, 96 hr, 4.5 μL each was collected and preserved at −80° C. Thereafter, 0.5 μL of protease K (6 mg/mL) was added to each of the thawed samples and they were stood at 37° C. for 10 min. Furthermore, 25.5 μL of a reaction quenching solution (8M urea, 10 mM EDTA: ethylenediaminetetraacetic acid, 0.05% BPB: bromophenol blue) was added and the mixtures were heat-treated at 95° C. for 10 min. Each sample was electrophoresised on acrylamide gel in the presence of 8M urea to separate aptamer contained in the sample. The gel was stained with SYBR Green II (Takara Bio Inc.) for 30 min, and the fluorescence of RNA was detected by Storm840 Phosphorimager (GE Healthcare Japan). From the obtained images, the band of intact aptamer was quantified, and the half-life was calculated and the stability of each sample was evaluated. The half-life of each sample is shown in the following Table 14. In Table 14, in addition to the above-mentioned conventionally-known aptamer against IL-17 (aptamer No. 50), other IL-17 aptamer described in WO 2010/008001 was produced and used for comparison with the aptamer of the present invention. The sequence of the produced aptamer is as described below.

Aptamer No. 51:
GGGGu(F)agc(F)c(F)ggaggagu(F)c(F)agu(F)aau(F)c(F)ggu(F)aCCCC) (SEQ ID NO: 51).

TABLE 14

Half-life of aptamer in human serum

| | time with PEG (hr) | time without PEG (hr) |
|---|---|---|
| aptamer No. 50 | 9.78 | 8.22 |
| aptamer No. 51 | 9.59 | 6.17 |
| aptamer No. 8 | 57.28 | 30.14 |
| aptamer No. 25 | 19.92 | 14.91 |
| aptamer No. 28 | 25.30 | 16.86 |
| aptamer No. 37 | 22.50 | 13.03 |
| aptamer No. 38 | 23.74 | 11.73 |
| aptamer No. 41 | 38.72 | 17.33 |
| aptamer No. 45 | 52.12 | 20.09 |
| aptamer No. 47 | 37.27 | 26.87 |
| aptamer No. 48 | 30.27 | 26.06 |

As a result of the measurement, all the newly altered-modified aptamers showed about 2 to 5-fold prolonged half-life in serum as compared to the conventionally-known aptamers (aptamer Nos. 50 and 51). Furthermore, prolongation of half-life by PEG modification was more remarkable in the newly altered-modified aptamers.

From the foregoing, it has been shown that the aptamer of the present invention significantly improves stability in serum as compared to conventionally-known aptamers.

Example 6: Serum Stability Test II

To mouse serum, human serum or phosphate buffer (33 μL) was added the aptamer produced in Example 1-1 or 1-2 (100 μM 2.5 μL), and the mixture was stood at 37° C. for 24 hr. After that, 4 μL was collected and added to 24 μL of a reaction quenching solution (8M urea, 10 mM EDTA: ethylenediaminetetraacetic acid, 0.05% BPB: bromophenol blue). After preservation at −70° C., each sample was electrophoresised on acrylamide gel in the presence of 8M urea to separate aptamer contained in the sample. The gel was stained with SYBR Green II (Takara Bio Inc.) for 30 min, and the fluorescence of RNA was detected by MOLECULAR IMAGER FX (BIO-RAD). From the obtained images, the band of intact aptamer was quantified using Science Lab 2005 Multi Gauge Ver3.0 manufactured by Fujifilm for the band corresponding to the residual aptamer, and the residual amount of each analyte in the serum was measured based on the results obtained with phosphate buffer as 100%.

TABLE 15

| | residual amount in mouse serum (%) 24 hr later |
|---|---|
| aptamer No. 50 | 7.3 |
| aptamer No. 51 | 5.5 |
| aptamer No. 8 | 17.1 |
| aptamer No. 48 | 17.3 |
| aptamer No. 56 | 17.0 |
| aptamer No. 57 | 14.6 |
| aptamer No. 58 | 28.4 |
| aptamer No. 59 | 59.4 |
| aptamer No. 60 | 43.4 |
| aptamer No. 61 | 22.3 |
| aptamer No. 62 | 81.5 |
| aptamer No. 63 | 49.5 |
| aptamer No. 64 | 94.7 |
| aptamer No. 65 | 48.6 |
| aptamer No. 66 | 49.1 |
| aptamer No. 67 | 87.0 |
| aptamer No. 68 | 63.9 |
| aptamer No. 69 | 76.8 |
| aptamer No. 70 | 89.0 |
| aptamer No. 71 | 83.7 |
| aptamer No. 72 | 32.3 |
| aptamer No. 73 | 65.3 |
| aptamer No. 74 | 33.9 |
| aptamer No. 75 | 44.4 |
| aptamer No. 76 | 66.6 |
| aptamer No. 77 | 50.8 |
| aptamer No. 78 | 36.6 |
| aptamer No. 79 | 26.8 |
| aptamer No. 80 | 66.2 |
| aptamer No. 81 | 86.8 |
| aptamer No. 82 | 67.7 |
| aptamer No. 83 | 76.9 |
| aptamer No. 84 | 82.9 |
| aptamer No. 85 | 86.1 |
| aptamer No. 86 | 79.9 |
| aptamer No. 87 | 81.1 |
| aptamer No. 88 | 84.2 |
| aptamer No. 89 | 92.4 |
| aptamer No. 90 | 95.4 |
| aptamer No. 91 | 78.6 |
| aptamer No. 92 | 79.9 |
| aptamer No. 93 | 66.8 |
| aptamer No. 94 | 64.4 |

TABLE 16

| | residual amount in human serum (%) 24 hr later |
|---|---|
| aptamer No. 50 | 24.9 |
| aptamer No. 51 | 29.0 |
| aptamer No. 8 | 76.6 |
| aptamer No. 48 | 57.7 |
| aptamer No. 56 | 48.4 |
| aptamer No. 58 | 37.2 |
| aptamer No. 59 | 57.1 |
| aptamer No. 60 | 48.4 |
| aptamer No. 61 | 52.1 |
| aptamer No. 62 | 59.6 |
| aptamer No. 63 | 57.8 |
| aptamer No. 64 | 90.4 |
| aptamer No. 65 | 68.2 |
| aptamer No. 66 | 57.9 |
| aptamer No. 67 | 107.9 |
| aptamer No. 68 | 90.1 |
| aptamer No. 69 | 36.1 |
| aptamer No. 71 | 79.7 |
| aptamer No. 73 | 91.4 |
| aptamer No. 76 | 31.7 |
| aptamer No. 80 | 52.7 |
| aptamer No. 81 | 98.9 |
| aptamer No. 82 | 51.1 |
| aptamer No. 83 | 81.3 |
| aptamer No. 84 | 89.1 |
| aptamer No. 85 | 80.8 |
| aptamer No. 86 | 94.8 |
| aptamer No. 87 | 98.5 |
| aptamer No. 88 | 73.3 |
| aptamer No. 89 | 99.0 |
| aptamer No. 90 | 106.8 |
| aptamer No. 91 | 94.8 |
| aptamer No. 92 | 92.9 |
| aptamer No. 93 | 90.6 |
| aptamer No. 94 | 101.1 |

As a result of the measurement, all the newly altered-modified aptamers showed an increased residual amount 24 hr later as compared to the conventionally-known aptamers (aptamer Nos. 50 and 51). The most stable aptamer showed an about 15-fold increased residual amount in serum 24 hr later.

From the foregoing, it has been shown that the aptamer of the present invention significantly improves stability in serum as compared to conventionally-known aptamers.

Example 7: Mouse Pharmacokinetics Test

An aptamer was dissolved in saline at 1 mg/mL, and intravenously administered to male C57BL/6 mouse (8-week-old, Charles River) at the dose of 1 mg/kg. The blood was collected 5, 15, 30 min later, 1, 2, 4, 6, 8, 24 hr later, or 48, 72, 96 hr later. The plasma was separated and preserved at −70° C. and, as for the aptamer of the present invention, the concentration of residual nucleic acid in plasma was measured according to the method reported by Judith M. Healy et al., (Pharmaceutical Research, December 2004, Volume 21, Issue 12, pp 2234-2246) and using the ELOSA method (hybridization method).

TABLE 17

| Half-life in mouse blood | |
|---|---|
| | $t_{1/2}$ (hr) |
| aptamer No. 50 | 1.79 |
| aptamer No. 51 | 0.85 |
| aptamer No. 8 | 6.38 |
| aptamer No. 48 | 4.29 |

TABLE 17-continued

Half-life in mouse blood

| | $t_{1/2}$ (hr) |
|---|---|
| aptamer No. 9 | 3.50 |
| aptamer No. 57 | 3.12 |
| aptamer No. 58 | 4.24 |
| aptamer No. 64 | 9.26 |

As a result of the measurement, all the newly altered-modified aptamers showed about 2 to 5-fold increased half-life as compared to the conventionally-known aptamers (aptamer Nos. 50 and 51).

From the foregoing, it has been shown that the stability of the aptamer of the present invention in blood significantly improved as compared to conventionally-known aptamers.

Example 8: IL-17 Inhibitory Effect of the Aptamer of the Present Invention in Mouse Air Pouch Inflammation Model Whether an altered-modified aptamer can inhibit biological activity of IL-17 in vivo was confirmed with mouse air pouch inflammation model by reference to Biochemical Pharmacology 77, 878-887 (2009).

In the mouse air pouch inflammation model, male C57BL/6J mice (7-week-old, Charles River) were used (n=4 or 5). The back was shaved and, the next day and 4 days later, air (2.5 mL) was subcutaneously injected into the back. At 3 days from the second air injection, a pegylated aptamer of the present invention was intraperitoneally administered by the method described in Example 5 and, 1 hr later, 2% aqueous carbomethylcellulose solution containing IL-17 (0.5 mg) was injected into air pouch to induce IL-6 production. The exudate in the air pouch was collected 24 hr after IL-17 injection, and the amount of IL-6 in the exudate was measured by ELISA. The IL-6 production inhibition ratio (%) is calculated, and results are shown in Tables 18 and 19 below. In Tables 18 and 19, a conventionally-known aptamers against IL-17 (aptamer Nos. 50 and 51) were used for comparison with the aptamer of the present invention.

TABLE 18

Inhibitory effects of various aptamers on IL-6 production at the dose of 10 mg/kg

| 10 mg/kg administration | IL-6 production inhibition ratio (%) |
|---|---|
| aptamer No. 50 | 50.20 |
| aptamer No. 51 | 42.86 |
| aptamer No. 8 | 88.16 |

TABLE 19

Inhibitory effects of various aptamers on IL-6 production at dose of 1 mg/kg

| 1 mg/kg administration | IL-6 production inhibition ratio (%) |
|---|---|
| aptamer No. 50 | 17.48 |
| aptamer No. 51 | 22.74 |
| aptamer No. 8 | 70.05 |
| aptamer No. 9 | 42.77 |
| aptamer No. 16 | 49.20 |
| aptamer No. 21 | 36.20 |
| aptamer No. 22 | 40.98 |
| aptamer No. 23 | 47.33 |

TABLE 19-continued

Inhibitory effects of various aptamers on IL-6 production at dose of 1 mg/kg

| 1 mg/kg administration | IL-6 production inhibition ratio (%) |
|---|---|
| aptamer No. 24 | 32.45 |
| aptamer No. 25 | 41.94 |
| aptamer No. 26 | 56.05 |
| aptamer No. 27 | 52.97 |
| aptamer No. 28 | 33.29 |
| aptamer No. 37 | 36.68 |
| aptamer No. 38 | 45.28 |
| aptamer No. 45 | 81.74 |
| aptamer No. 46 | 72.84 |
| aptamer No. 47 | 63.03 |
| aptamer No. 48 | 67.50 |
| aptamer No. 49 | 32.21 |

As a result of the measurement, it was confirmed that all the newly altered-modified aptamers had about 2- to 5-fold higher IL-6 production inhibition ratio, compared to the conventionally-known aptamers (aptamer Nos. 50 and 51) when they had been administered at the same concentration. Furthermore, it was confirmed that even when the administration concentration of the conventionally-known aptamers (aptamer Nos. 50 and 51) was increased 10-fold, the IL-6 production inhibition ratio of the altered-modified aptamer was higher and the IL-17 inhibitory activity of the aptamer of the present invention remarkably increased also in vivo.

Example 9-1: Anti-Inflammatory Effect on IL-23-Induced Psoriasis Model in Mice—1

According to the method reported by Heather L. Rizzo et al., (J Immunol. 186, 1495-1502 (2011)), a suppressive effect of the aptamer of the present invention on IL-23-induced psoriasis model was examined.

First, PBS (20 μL) containing 0.1% bovine serum albumin alone was intradermally administered to the left auricle and mouse IL-23 (eBioscience, 1 μg/20 μL) was intradermally administered to the right auricle of a male C57BL/6 mouse (7-week-old, Charles River) once per day for 4 consecutive days. Thereafter, the aptamer of the present invention pegylated by the method described in Example 5 (aptamer No. 8) (5 mg/kg) was intraperitoneally administered once a day, every day. As a positive control, anti-IL-17 antibody (eBioscience, 100 μg/head) was intraperitoneally administered once a day, every other day and, as a negative control, saline (10 mL/kg) was intraperitoneally administered once a day, every day. After 24 hr from the final administration of mouse IL-23, the thickness of the both auricle was measured by Dial Thickness Gauge (G-1A, PEACOCK), and the efficacy of the aptamer of the present invention for psoriasis-like dermatitis was evaluated.

Figure 2:
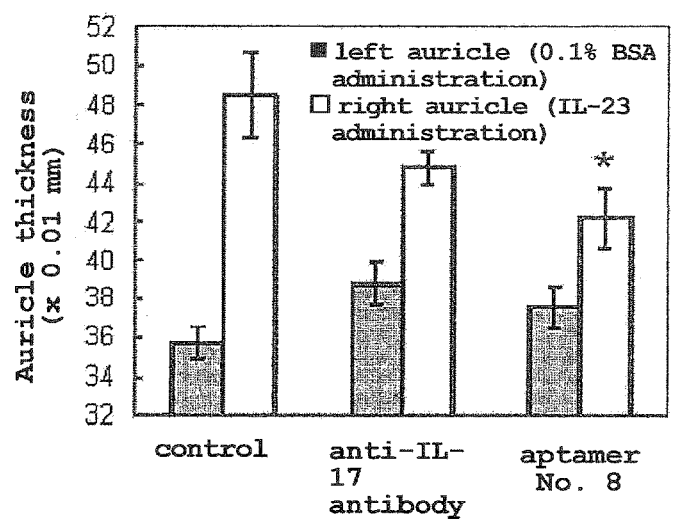
FIG. 2 shows a suppressing effect of a pegylated aptamer of the present invention on mouse IL-23-induced psoriasis model, wherein the horizontal axis shows saline administration group (negative control group), anti-IL-17 antibody administration group (positive control group), and pegylated aptamer (A: aptamer No. 8; B: aptamer No. 51 and aptamer No. 48) administration group, and the vertical axis shows the thickness of mouse auricle. In the Figure, each value shows mean±standard error of the mean (n=4 or 5), and a statistically significant difference was analyzed by one-way analysis of variance and the Dunnett's method (*:P<0.05).
Figure 2:
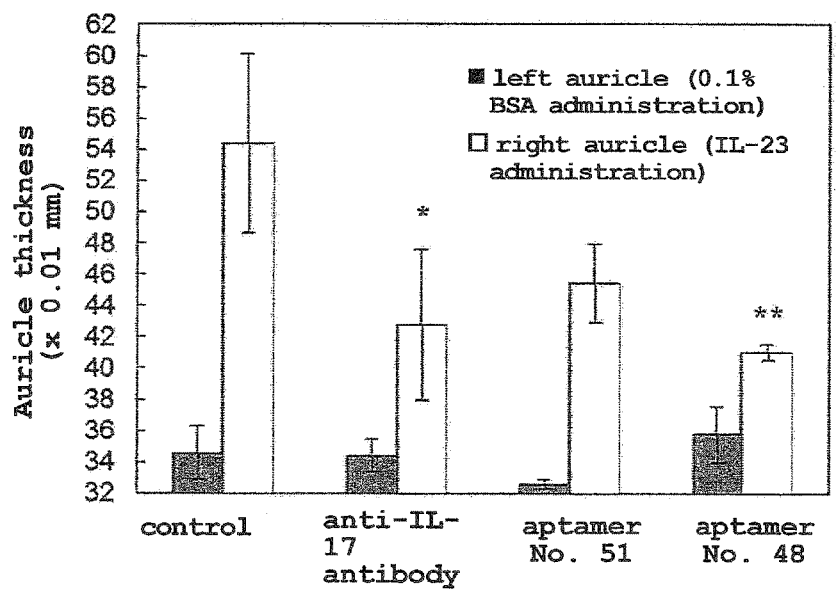

The thickness of the auricle in the pegylated aptamer of the present invention (aptamer No. 8) administration group significantly decreased as compared to that of the negative control group administered with saline (FIG. 2A). In the anti-IL-17 antibody administration group used as a positive control, a remarkable effect could not be confirmed at the dose used in this study. In the Figure, each value shows mean±standard error of mean (n=4 or 5), and a statistically significant difference was analyzed by one-way analysis of variance and Dunnett's method (*:P<0.05).

The above results strongly suggest that the aptamer of the present invention against IL-17 can be utilized as a therapeutic drug for immune dermatosis diseases such as psoriasis.

Example 9-2: Anti-Inflammatory Effect on IL-23-Induced Psoriasis Model in Mice—2

According to the method reported by Heather L. Rizzo et al., (J Immunol. 186, 1495-1502 (2011)), a suppressive effect of the aptamer of the present invention on IL-23-induced psoriasis model was examined.

That is, PBS (20 μL) containing 0.1% bovine serum albumin was intradermally administered to the left auricle and mouse IL-23 (eBioscience, 1 μg/20 μL) was intradermally administered to the right auricle of a male C57BL/6 mouse (7-week-old, Charles River) once per day for 4 consecutive days. Thereafter, the aptamer of the present invention pegylated by the method described in Example 5 (aptamer No. 48) (10 mg/kg) and a conventionally-known aptamer pegylated by a similar method (aptamer No. 51) (10 mg/kg) were intraperitoneally administered once a day for 5 consecutive days from one day before intradermal administration. As a positive control, anti-IL-17 antibody (eBioscience, 100 μg/head) was intraperitoneally administered once a day every other day from the day of the intradermal administration and, as a negative control, saline (10 mL/kg) was intraperitoneally administered once a day for 5 consecutive days from one day before the intradermal administration. After 24 hr from the final administration of mouse IL-23, the thickness of the both auricles was measured by Dial Thickness Gauge (G-1A, PEACOCK), and the efficacy of the aptamer of the present invention for psoriasis-like dermatitis was evaluated.

The thickness of the auricle in the pegylated aptamer of the present invention (aptamer No. 48) administration group and anti-IL-17 antibody administration group significantly decreased as compared to that of the negative control group administered with saline, but the auricle thickness of the pegylated conventionally-known aptamer (aptamer No. 51) administration group did not show a significant difference (FIG. 2B). In the Figure, each value shows mean±standard error of mean (n=5), and a statistically significant difference was analyzed by one-way analysis of variance and Dunnett's method (*:P<0.05, **:P<0.01).

The above results strongly suggest that the aptamer of the present invention against IL-17 can be utilized as a therapeutic drug for immune-related skin diseases such as psoriasis.

Example 10: Anti-Inflammatory Effect on Glucose-6-Phosphate Isomerase-Induced Arthritis Model in Mice According to the method reported by A Ishiguro et al., (Arthritis Rheum. 63, 455-466 (2011)), the suppressive effect of the aptamer of the present invention on glucose-6-phosphate isomerase (GPI)-induced arthritis model was examined.

First, a male DBA/1 mouse (8-week-old, Charles River) was intradermally administered at the base of tail with mouse GPI (300 μg/head) emulsified with complete adjuvant (Difco), and the dosing of the aptamer of the present invention pegylated by the method described in Example 5 (aptamer No. 8) (5 mg/kg) was started. The aptamer was intraperitoneally administered once a day, every other day. As a control, saline was intraperitoneally administered once a day at dose of 10 mL/kg every other day. The animal was observed every day, the inflammation of each paw was scored in 3 levels from 0 (no symptom) to 2 (redness of whole limb and maximum tumentia), and the efficacy of the aptamer of the present invention on arthritis was evaluated.

Figure 3:
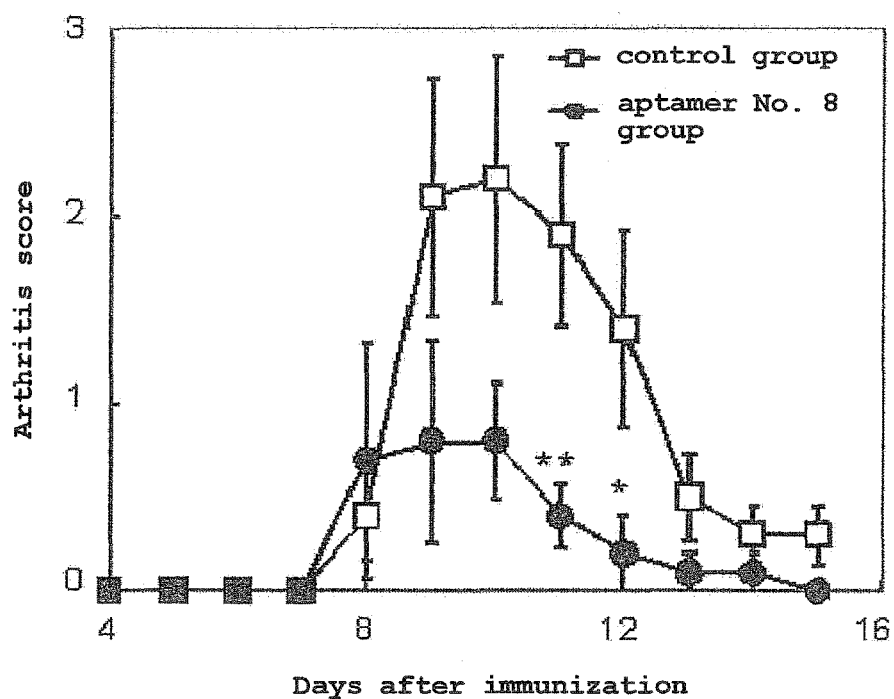
FIG. 3 shows an arthritis suppressing effect of a pegylated aptamer of the present invention on glucose-6-phosphate isomerase-induced arthritis model in mice. In the Figure, open square shows saline administration group (control group), and closed circle shows pegylated aptamer (aptamer No. 8) administration group. In the Figure, each value shows mean±standard error of the mean (n=10), and a statistically significant difference was analyzed by the Wilcoxon-Mann-Whitney's method (*:P<0.05, **:P<0.01).

Compared to the control group administered with saline, the arthritis score of the pegylated aptamer of the present invention (aptamer No. 8) administration group significantly decreased (day 11 and day 12 after immunization, FIG. 3). In the Figure, each value shows mean±standard error of the mean (n=10), and a statistically significant difference was analyzed by the Wilcoxon-Mann-Whitney's method (*:P<0.05, **:P<0.01).

The above results strongly suggest that the aptamer of the present invention against IL-17 can be utilized as a therapeutic drug for autoimmune-related arthritis such as rheumatoid arthritis.

Example 11-1: Anti-Inflammatory Effect on Collagen-Induced Arthritis Model in Mice—1

According to the method reported by S Toyama et al., (Arthritis Res Ther 12, R92 (2010)), the suppressive effect of the aptamer of the present invention on collagen-induced arthritis model was examined.

First, a male DBA/1 mouse (8-week-old, Charles River) was intradermally administered at the base of tail with bovine Type II collagen (200 μg/head, Collagen Research Center) emulsified with complete adjuvant (Chondrex) (day 1 of experiment). On day 22 of the experiment, the mouse was boosted with bovine Type II collagen emulsified with incomplete adjuvant as well as an aptamer of the present invention pegylated by the method described in Example 5 (aptamer No. 8) (5 mg/kg) was intraperitoneally administered once per day for 16 consecutive days. As a control, saline was intraperitoneally administered once per day at the dose of 10 mL/kg every day. The animal was observed every day, the inflammation of each paw was scored in 5 levels from 0 (no symptom) to 4 (redness of whole limb and maximum tumentia), and the efficacy of the aptamer of the present invention on arthritis was evaluated.

Figure 4:
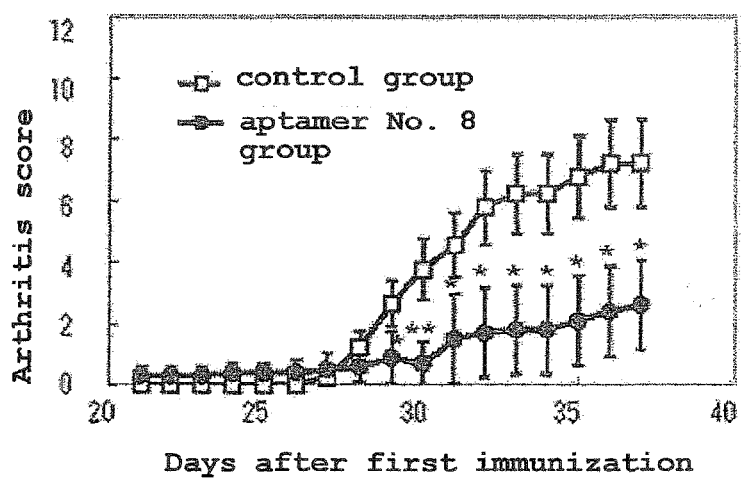
FIG. 4 shows an arthritis suppressing effect of a pegylated aptamer of the present invention on collagen-induced arthritis model in mice. In the Figure, open square shows saline administration group (control group), closed circle shows pegylated aptamer of the present invention (A: aptamer No. 8; B: aptamer No. 64) administration group, and black diamond shows known aptamer (aptamer No. 51) administration group. In the Figure, each value shows mean±standard error of the mean (n=9 or 10), and a statistically significant difference was analyzed by the Wilcoxon-Mann-Whitney's method (*:P<0.05, **:P<0.01).
Figure 4:
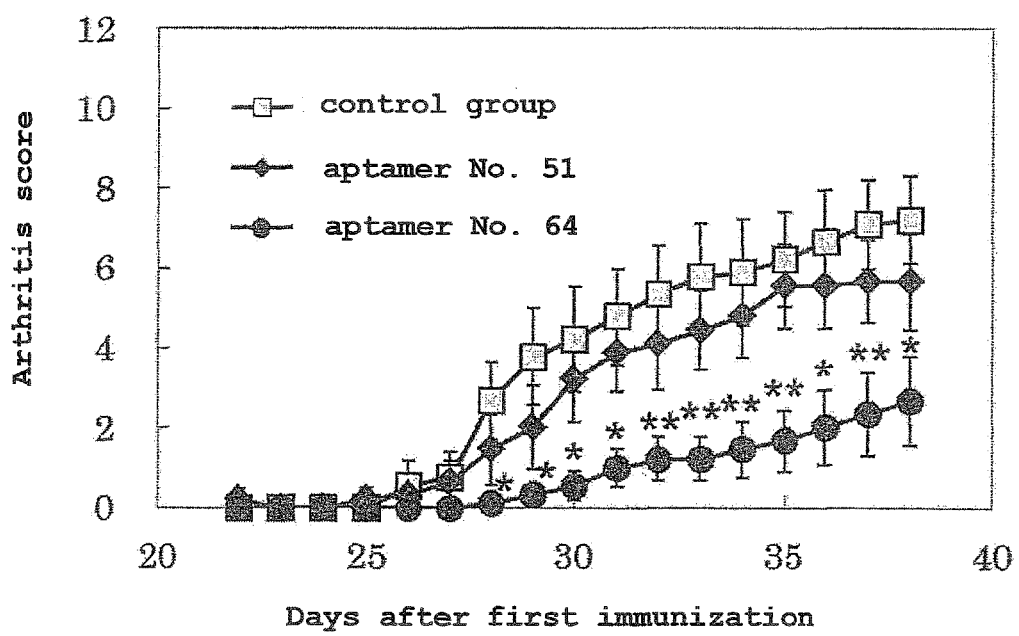

Compared to the control group administered with saline, the arthritis score of the pegylated aptamer of the present invention (aptamer No. 8) administration group significantly decreased (FIG. 4A). In the Figure, each value shows mean±standard error of the mean (n=9 or 10), and a statistically significant difference was analyzed by the Wilcoxon-Mann-Whitney's method (*:P<0.05, **:P<0.01).

Example 11-2: Anti-Inflammatory Effect on Collagen-Induced Arthritis Model in Mice—2

By a method similar to that in Example 11-1, the suppressive effect of the aptamer of the present invention on collagen-induced arthritis model was examined. As the aptamer of the present invention, an aptamer of the present invention pegylated by the method described in Example 5 (aptamer No. 64) (5 mg/kg) and a conventionally-known aptamer pegylated by a similar method (aptamer No. 51) (5 mg/kg) were used and, as a control, saline was intraperitoneally administered once a day at dose of 10 mL/kg for 16 consecutive days.

As compared to the control group administered with saline, the arthritis score of the pegylated aptamer of the present invention (aptamer No. 64) administration group significantly decreased. However, the arthritis score of the pegylated conventionally-known aptamer (aptamer No. 51) administration group did not show a significant difference (FIG. 4B). In the Figure, each value shows mean±standard error of the mean (n=9), and a statistically significant difference was analyzed by Wilcoxon-Mann-Whitney's method (*:P<0.05, **:P<0.01).

Since both the GPI-induced arthritis model (Example 10) and collagen-induced arthritis model (Examples 11-1 and 11-2), widely used as animal models for arthritis, demonstrated the effectiveness of the aptamer of the present invention, it was further confirmed that the aptamer of the present invention against IL-17 can be utilized as a therapeutic drug for autoimmune related arthritis such as rheumatoid arthritis. Particularly, it was clarified that the aptamer of the present invention shows a stronger activity than conventionally-known aptamers.

INDUSTRIAL APPLICABILITY

The aptamer or the complex of the present invention can be useful as a medicament or reagent such as a diagnostic reagent for a disease including inflammatory disease, autoimmune disease, cancer, allergy or infection, and the like. The aptamer or the complex of the present invention can also be useful in purifying and concentrating IL-17, labeling of IL-17, and detecting and quantifying IL-17.

This application is based on a patent application No. 2013-060817 filed in Japan (filing date: Mar. 22, 2013), the contents of which are incorporated in full herein.

The invention claimed is:

1. An aptamer comprising a sequence represented by the following formula (Ia), which binds to IL-17 to inhibit binding of IL-17 and IL-17 receptor:

g(M)g(M)g(M)u(M)a'(M)g'(X1)c(M)c(M)g'g(M)a'(X4)g(X5)g(M)a(M)g(X5)u'(F)c(X7)a'(X2)g(X6)u'(F)r(X3)a'(X3)u(M)c(M)g(M)g(M)u'(X7)a'(M)c'(M)c'(M)c'(M) (SEQ ID NO: 95)

wherein a, g, c and u are each an RNA wherein the base is adenine, guanine, cytosine and uracil, respectively, r is an RNA wherein the base is adenine or guanine, a', g' and c' are each an RNA or DNA wherein the base is adenine, guanine and cytosine, respectively, u' is an RNA wherein the base is uracil, a DNA wherein the base is uracil or a DNA wherein the base is thymine, parentheses in nucleotide indicate modification of the nucleotide, (M) indicates that, when the nucleotide is an RNA, a hydroxyl group at the 2'-position of ribose therein is substituted by an O-methyl group, (F) indicates that, when the nucleotide is an RNA, a hydroxyl group at the 2'-position of ribose therein is substituted by a fluorine atom, (X1) indicates that nucleotide is non-modified or phosphorothioated, or when the nucleotide is an RNA, a hydroxyl group at the 2'-position of ribose therein is substituted by a fluorine atom, (X2) indicates that nucleotide is non-modified, or when the nucleotide is an RNA, a hydroxyl group at the 2'-position of ribose therein is substituted by a fluorine atom, (X3) indicates that nucleotide is non-modified, or when the nucleotide is an RNA, a hydroxyl group at the 2'-position of ribose therein is substituted by an O-methyl group, (X4) indicates that nucleotide is non-modified, or when the nucleotide is an RNA, a hydroxyl group at the 2'-position of ribose therein is substituted by a fluorine atom or an O-methyl group, (X5) indicates that nucleotide is non-modified or phosphorothioated, (X6) indicates that nucleotide is non-modified or phosphorothioated, or when the nucleotide is an RNA, a hydroxyl group at the 2'-position of ribose therein is substituted by an O-methyl group, and (X7) indicates that when nucleotide is an RNA, a hydroxyl group at the 2'-position of ribose therein is substituted by a fluorine atom or an O-methyl group.

2. The aptamer according to claim 1, comprising a sequence represented by the following formula (Ia'):

g(M)g(M)g(M)u(M)a'(M)g(X5)c(M)c(M)Gg(M)a(X4)gg(M)a(M)g(X5)u'(F)c(X7)a(X2)g(X5)u'(F)r(X3)a(X3)u(M)c(M)g(M)g(M)u(X7)a(M)c'(M)c'(M)c'(M) (SEQ ID NO: 96)

wherein a, g, c, u and r, a', c' and u', as well as (M), (F) and (X2)-(X5) and (X7) are as defined for the formula (Ia), and G is a DNA wherein the base is guanine.

3. The aptamer according to claim 1, comprising a sequence represented by the following formula (I):

g(M)g(M)g(M)u(M)a'(M)g'(X1)c(M)c(M)g'g(M)a'(X2)gg(M)a(M)gu'(F)c(F)a'(X2)gu'(F)a(X3)a'(X3)u(M)c(M)g(M)g(M)u'(F)a'(M)c'(M)c'(M)c'(M) (SEQ ID NO: 97)

wherein a, g, c and u, a', g', c' and u', as well as (M), (F) and (X1)-(X3) are as defined for the formula (Ia).

4. The aptamer according to claim 1, comprising a sequence represented by the following formula (Ia"):

g(M)g(M)g(M)u(M)a'(M)g(X5)c(M)c(M)Gg(M)a(X7)g(X5)g(M)a(M)g(X5)u'(F)c(X7)a(F)g(X6)u'(F)r(X3)a(X3)u(M)c(M)g(M)g(M)u(X7)a'(M)c'(M)c'(M)c'(M) (SEQ ID NO: 98)

wherein a, g, c, u and r, a', c' and u', as well as (M), (F), (X3) and (X5)-(X7) are as defined for the formula (Ia), and G is a DNA wherein the base is guanine.

5. The aptamer according to claim 4, wherein, in the formula (Ia"), c'(M)c'(M)c'(M) on the 3'-terminal side is c(M)c(M)c(M).

6. The aptamer according to claim 1, comprising the sequence of any of SEQ ID NOs: 52-94.

7. The aptamer according to claim 1, comprising the sequence of any of SEQ ID NOs: 3-49.

8. The aptamer according to claim 1, having a base length of not more than 70.

9. An aptamer comprising a sequence represented by the following formula (II), which binds to IL-17 to inhibit binding of IL-17 and IL-17 receptor:

g(x1)g(x1)g(x1)u(F)ag(S)c(F)c(F)g'(S)g(x2)aggagu(F)c(F)agu(F)aau(F)c(F)ggu(F)ac'(x3)c'(x3)c'(x3) (SEQ ID NO: 99)

wherein a, g, c and u are each an RNA wherein the base is adenine, guanine, cytosine and uracil, respectively, g' and c' are each an RNA or DNA wherein the base is guanine or cytosine, respectively, parentheses in nucleotide indicate modification of the nucleotide, (F) indicates that a hydroxyl group at the 2'-position of ribose in the nucleotide is substituted by a fluorine atom, (S) indicates that, when nucleotide is an RNA, it is phosphorothioated, (x1) indicates that nucleotide is modified with Locked Nucleic Acid (LNA), or when the nucleotide is an RNA, a hydroxyl group at the 2'-position of ribose therein is substituted by an O-methyl group, (x2) indicates that nucleotide is non-modified, or when the nucleotide is an RNA, a hydroxyl group at the 2'-position of ribose therein is substituted by an O-methyl group, and (x3) indicates that nucleotide is non-modified, or modified with LNA.

10. The aptamer according to claim 9, comprising the sequence shown by SEQ ID NO: 1 or SEQ ID NO: 2.

11. The aptamer according to claim 9, having a base length of not more than 70.

12. The aptamer according to claim 1, which is modified with inverted dT or polyethylene glycol.

13. A complex comprising the aptamer according to claim 1 and a functional substance.

14. A medicament comprising the aptamer according to claim 1 or a complex comprising the aptamer and a functional substance.

15. A diagnostic reagent comprising the aptamer according to claim 1 or a complex comprising the aptamer and a functional substance.

16. A detection probe comprising the aptamer according to claim 1 or a complex comprising the aptamer and a functional substance.

17. A carrier for IL-17 purification, comprising the aptamer according to claim 1 or a complex comprising the aptamer and a functional sub stance.

18. A method of detecting IL-17, comprising using the aptamer according to claim 1 or a complex comprising the aptamer and a functional sub stance.

19. A method of purifying IL-17, comprising using the aptamer according to claim 1 or a complex comprising the aptamer and a functional substance.

20. A method of treating or preventing a disease, comprising administering an effective amount of the aptamer according to claim 1 or a complex comprising the aptamer and a functional substance to a mammal in need thereof.

21. The method according to claim 20, wherein the mammal is a human.

* * * * *

SEQUENCE LISTING

```
<160> NUMBER OF SEQ ID NOS: 99

<210> SEQ ID NO 1
<211> LENGTH: 31
<212> TYPE: RNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(3)
<223> OTHER INFORMATION: Modification with LNA
<220> FEATURE:
<221> NAME/KEY: misc_feature
<222> LOCATION: (4)..(4)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (9)..(9)
<223> OTHER INFORMATION: Nucleotide is phosphorothioated.
<220> FEATURE:
<221> NAME/KEY: misc_feature
<222> LOCATION: (16)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (23)..(24)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (29)..(31)
<223> OTHER INFORMATION: LNA wherein the base is methylcytosine.

<400> SEQUENCE: 1
ggguagccgg aggagucagu aaucgguacc c                                 31
```

```
<210> SEQ ID NO 2
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(3)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (4)..(4)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(28)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (23)..(24)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (29)..(31)
<223> OTHER INFORMATION: deoxyribonucleotide

<400> SEQUENCE: 2
``` gggguagccgg aggagucagu aaucgguacc c                                    31

<210> SEQ ID NO 3
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(27)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: deoxyribonucleotide -continued

<400> SEQUENCE: 3
ggguagccgg aggagucagu aaucgguacc c                                   31

<210> SEQ ID NO 4
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(28)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:

```
<221> NAME/KEY: misc_feature
<222> LOCATION: (21)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 4
ggguagccgg aggagucagu aaucgguacc c                                31

<210> SEQ ID NO 5
<211> LENGTH: 33
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(9)
<223> OTHER INFORMATION: ribonucleotide
<220> FEATURE:
<221> NAME/KEY: misc_feature
<222> LOCATION: (1)..(6)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (7)..(7)
<223> OTHER INFORMATION: Nucleotide is phosphorothioated.
<220> FEATURE:
<221> NAME/KEY: misc_feature
<222> LOCATION: (8)..(9)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (10)..(10)
<223> OTHER INFORMATION: deoxyribonucleotide
<220> FEATURE:
<221> NAME/KEY: misc_feature
<222> LOCATION: (11)..(16)
<223> OTHER INFORMATION: ribonucleotide
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (12)..(12)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (14)..(15)
<223> OTHER INFORMATION: When the nucleotide is a ribonucleotide, a
      hydroxyl group at the 2'-position of ribose therein
      is substituted by an O-methyl group.
```

```
<220> FEATURE:
<221> NAME/KEY: misc_feature
<222> LOCATION: (17)..(17)
<223> OTHER INFORMATION: deoxyribonucleotide
<220> FEATURE:
<221> NAME/KEY: misc_feature
<222> LOCATION: (18)..(20)
<223> OTHER INFORMATION: ribonucleotide
<220> FEATURE:
<221> NAME/KEY: misc_feature
<222> LOCATION: (18)..(19)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(21)
<223> OTHER INFORMATION: deoxyribonucleotide
<220> FEATURE:
<221> NAME/KEY: misc_feature
<222> LOCATION: (22)..(28)
<223> OTHER INFORMATION: ribonucleotide
<220> FEATURE:
<221> NAME/KEY: misc_feature
<222> LOCATION: (22)..(27)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (29)..(33)
<223> OTHER INFORMATION: deoxyribonucleotide

<400> SEQUENCE: 5
gggguagccg gaggagtcag taaucgguac ccc                                    33

<210> SEQ ID NO 6
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
```

```
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(27)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: deoxyribonucleotide

<400> SEQUENCE: 6
ggguagccgg aggagtcagt aaucgguacc c                                    31

<210> SEQ ID NO 7
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
```

```
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(28)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (29)..(31)
<223> OTHER INFORMATION: deoxyribonucleotide
```

<400> SEQUENCE: 7
ggguagccgg aggagucagu aaucgguacc c          31

<210> SEQ ID NO 8
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.

```
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein
      is substituted by an O-methyl
      group.
<220> FEATURE:
<221> NAME/KEY: misc_feature
<222> LOCATION: (29)..(31)
<223> OTHER INFORMATION: deoxyribonucleotide

<400> SEQUENCE: 8
ggguagccgg aggagtcagt aaucgguacc c                                     31

<210> SEQ ID NO 9
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl
      group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
```

```
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 9
ggguagccgg aggagtcagt aaucgguacc c                                  31

<210> SEQ ID NO 10
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
```

```
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(27)
<223> OTHER INFORMATION: ribonucleotide
<220> FEATURE:
```

<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: deoxyribonucleotide

<400> SEQUENCE: 10
ggguagccgg aggagtcagt aaucgguacc c                             31

<210> SEQ ID NO 11
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a hydroxyl group at the 2'-position of ribose therein
   is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
   hydroxyl group at the 2'-position of ribose therein is
   substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
   hydroxyl group at the 2'-position of ribose therein
   is substituted by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
   hydroxyl group at the 2'-position of ribose therein
   is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
   hydroxyl group at the 2'-position of ribose therein is
   substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
   hydroxyl group at the 2'-position of ribose therein
   is substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 11
ggguagccgg aggagtcagt aaucgguacc c                                      31

<210> SEQ ID NO 12
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)

```
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
```

<222> LOCATION: (28)..(28)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 12
ggguagccgg aggagtcagt aaucgguacc c                                    31

<210> SEQ ID NO 13
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:

```
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 13
ggguagccgg aggagtcagt aaucgguacc c                                    31

<210> SEQ ID NO 14
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
```

```
<220> FEATURE:
<221> NAME/KEY: misc_feature
<222> LOCATION: (6)..(6)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein
      is substituted by an O-methyl group.
<220> FEATURE:
```

<221> NAME/KEY: misc_feature
<222> LOCATION: (29)..(31)
<223> OTHER INFORMATION: deoxyribonucleotide

<400> SEQUENCE: 14
ggguagccgg aggagtcagt aaucgguacc c                              31

<210> SEQ ID NO 15
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide

```
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 15 gggutagccgg aggagtcagt aaucgguacc c                                    31

<210> SEQ ID NO 16
<211> LENGTH: 33
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(5)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (6)..(6)
<223> OTHER INFORMATION: deoxyribonucleotide
<220> FEATURE:
<221> NAME/KEY: misc_feature
<222> LOCATION: (7)..(9)
```

```
<223> OTHER INFORMATION: ribonucleotide
<220> FEATURE:
<221> NAME/KEY: misc_feature
<222> LOCATION: (7)..(7)
<223> OTHER INFORMATION: Nucleotide is phosphorothioated.
<220> FEATURE:
<221> NAME/KEY: misc_feature
<222> LOCATION: (8)..(9)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (10)..(10)
<223> OTHER INFORMATION: deoxyribonucleotide
<220> FEATURE:
<221> NAME/KEY: misc_feature
<222> LOCATION: (11)..(16)
<223> OTHER INFORMATION: ribonucleotide
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (12)..(12)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (14)..(15)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (17)..(17)
<223> OTHER INFORMATION: deoxyribonucleotide
<220> FEATURE:
<221> NAME/KEY: misc_feature
<222> LOCATION: (18)..(20)
<223> OTHER INFORMATION: ribonucleotide
<220> FEATURE:
<221> NAME/KEY: misc_feature
<222> LOCATION: (18)..(19)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(21)
<223> OTHER INFORMATION: deoxyribonucleotide
<220> FEATURE:
<221> NAME/KEY: misc_feature
<222> LOCATION: (22)..(29)
<223> OTHER INFORMATION: ribonucleotide
<220> FEATURE:
<221> NAME/KEY: misc_feature
<222> LOCATION: (22)..(27)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (29)..(29)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
```

<222> LOCATION: (30)..(33)
<223> OTHER INFORMATION: deoxyribonucleotide

<400> SEQUENCE: 16
gggguagccg gaggagtcag taaucgguac ccc        33

<210> SEQ ID NO 17
<211> LENGTH: 33
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(5)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (6)..(6)
<223> OTHER INFORMATION: deoxyribonucleotide
<220> FEATURE:
<221> NAME/KEY: misc_feature
<222> LOCATION: (7)..(9)
<223> OTHER INFORMATION: ribonucleotide
<220> FEATURE:
<221> NAME/KEY: misc_feature
<222> LOCATION: (7)..(7)
<223> OTHER INFORMATION: Nucleotide is phosphorothioated.
<220> FEATURE:
<221> NAME/KEY: misc_feature
<222> LOCATION: (8)..(9)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (10)..(10)
<223> OTHER INFORMATION: deoxyribonucleotide
<220> FEATURE:
<221> NAME/KEY: misc_feature
<222> LOCATION: (11)..(16)
<223> OTHER INFORMATION: ribonucleotide
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (12)..(12)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (14)..(15)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (17)..(17)
<223> OTHER INFORMATION: deoxyribonucleotide
<220> FEATURE:
<221> NAME/KEY: misc_feature
<222> LOCATION: (18)..(20)
<223> OTHER INFORMATION: ribonucleotide
<220> FEATURE:
<221> NAME/KEY: misc_feature
<222> LOCATION: (18)..(19)

<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(21)
<223> OTHER INFORMATION: deoxyribonucleotide
<220> FEATURE:
<221> NAME/KEY: misc_feature
<222> LOCATION: (22)..(22)
<223> OTHER INFORMATION: ribonucleotide
<220> FEATURE:
<221> NAME/KEY: misc_feature
<222> LOCATION: (22)..(22)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (23)..(23)
<223> OTHER INFORMATION: deoxyribonucleotide
<220> FEATURE:
<221> NAME/KEY: misc_feature
<222> LOCATION: (24)..(29)
<223> OTHER INFORMATION: ribonucleotide
<220> FEATURE:
<221> NAME/KEY: misc_feature
<222> LOCATION: (24)..(27)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (29)..(29)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (30)..(33)
<223> OTHER INFORMATION: deoxyribonucleotide

<400> SEQUENCE: 17
gggguagccg gaggagtcag taaucgguac ccc                                33

<210> SEQ ID NO 18
<211> LENGTH: 33
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(5)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (6)..(6)
<223> OTHER INFORMATION: deoxyribonucleotide
<220> FEATURE:
<221> NAME/KEY: misc_feature
<222> LOCATION: (7)..(9)
<223> OTHER INFORMATION: ribonucleotide
<220> FEATURE:
<221> NAME/KEY: misc_feature

```
<222> LOCATION: (7)..(7)
<223> OTHER INFORMATION: Nucleotide is phosphorothioated.
<220> FEATURE:
<221> NAME/KEY: misc_feature
<222> LOCATION: (8)..(9)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (10)..(10)
<223> OTHER INFORMATION: deoxyribonucleotide
<220> FEATURE:
<221> NAME/KEY: misc_feature
<222> LOCATION: (11)..(16)
<223> OTHER INFORMATION: ribonucleotide
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (12)..(12)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (14)..(15)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (17)..(17)
<223> OTHER INFORMATION: deoxyribonucleotide
<220> FEATURE:
<221> NAME/KEY: misc_feature
<222> LOCATION: (18)..(20)
<223> OTHER INFORMATION: ribonucleotide
<220> FEATURE:
<221> NAME/KEY: misc_feature
<222> LOCATION: (18)..(19)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(21)
<223> OTHER INFORMATION: deoxyribonucleotide
<220> FEATURE:
<221> NAME/KEY: misc_feature
<222> LOCATION: (22)..(29)
<223> OTHER INFORMATION: ribonucleotide
<220> FEATURE:
<221> NAME/KEY: misc_feature
<222> LOCATION: (24)..(27)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (29)..(29)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (30)..(33)
<223> OTHER INFORMATION: deoxyribonucleotide
```

<400> SEQUENCE: 18
gggguagccg gaggagtcag taaucgguac ccc                              33

<210> SEQ ID NO 19
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a

```
        hydroxyl group at the 2'-position of ribose therein is
        substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
        hydroxyl group at the 2'-position of ribose therein
        is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
        hydroxyl group at the 2'-position of ribose therein is
        substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
        hydroxyl group at the 2'-position of ribose therein
        is substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 19
ggguagccgg aggagtcagt aaucgguacc c                                31

<210> SEQ ID NO 20
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
        hydroxyl group at the 2'-position of ribose therein
        is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
        hydroxyl group at the 2'-position of ribose therein
        is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
```

```
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (29)..(31)
<223> OTHER INFORMATION: deoxyribonucleotide
```

<400> SEQUENCE: 20
ggguagccgg aggagtcagt aaucgguacc c                               31

<210> SEQ ID NO 21
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:

```
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein
      is substituted by an O-methyl group.

<400> SEQUENCE: 21
ggguagccgg aggagtcagt aaucggtacc c                               31

<210> SEQ ID NO 22
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
```

```
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein
      is substituted by an O-methyl group.

<400> SEQUENCE: 22
ggguagccgg aggagtcagt aaucggtacc c                                   31

<210> SEQ ID NO 23
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
```

```
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
      hydroxyl group at the 2'-position of ribose therein
      is substituted by an O-methyl group.

<400> SEQUENCE: 23
ggguagccgg aggagtcagt aaucggtacc c                                      31

<210> SEQ ID NO 24
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
```

```
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
```

```
<221> NAME/KEY: misc_feature
<222> LOCATION: (29)..(31)
<223> OTHER INFORMATION: When the nucleotide is a ribonucleotide, a
      hydroxyl group at the 2'-position of ribose therein
      is substituted by an O-methyl group.

<400> SEQUENCE: 24
ggguagccgg aggagtcagt aaucggtacc c                                         31

<210> SEQ ID NO 25
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
```

<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
    hydroxyl group at the 2'-position of ribose therein
    is substituted by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
    hydroxyl group at the 2'-position of ribose therein
    is substituted by an O-methyl group.
<220> FEATURE:
<221> NAME/KEY: misc_feature
<222> LOCATION: (27)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
    hydroxyl group at the 2'-position of ribose therein
    is substituted by an O-methyl group.

<400> SEQUENCE: 25
ggguagccgg aggagtcagt aaucggtacc c                                31

<210> SEQ ID NO 26
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
    hydroxyl group at the 2'-position of ribose therein
    is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
    hydroxyl group at the 2'-position of ribose therein
    is substituted by an O-methyl group.
<220> FEATURE:

```
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein
      is substituted by an O-methyl group.

<400> SEQUENCE: 26
ggguagccgg aggagtcagt aaucggtacc c                                  31

<210> SEQ ID NO 27
<211> LENGTH: 31
<212> TYPE: DNA
<213> ORGANISM: Artificial Sequence
```

```
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
```

<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein
      is substituted by an O-methyl group.

<400> SEQUENCE: 27
ggguagccgg aggagtcagt aaucggtacc c                                    31

<210> SEQ ID NO 28
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide

```
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein
      is substituted by an O-methyl group.

<400> SEQUENCE: 28
ggguagccgg aggagtcagt aaucggtacc c                                      31

<210> SEQ ID NO 29
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
```

```
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: deoxyribonucleotide
```

```
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein
      is substituted by an O-methyl group.

<400> SEQUENCE: 29
ggguagccgg aggagtcagt aaucggtacc c                                  31

<210> SEQ ID NO 30
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
```

```
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein
      is substituted by an O-methyl
      group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein
      is substituted by an O-methyl group.

<400> SEQUENCE: 30
ggguagccgg aggagtcagt aaucggtacc c                             31

<210> SEQ ID NO 31
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
```

-continued

```
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
```

-continued

```
<222> LOCATION: (29)..(31)
<223> OTHER INFORMATION: When the nucleotide is a ribonucleotide, a
      hydroxyl group at the 2'-position of ribose therein
      is substituted by an O-methyl group.

<400> SEQUENCE: 31
ggguagccgg aggagtcagt aaucggtacc c                              31

<210> SEQ ID NO 32
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
```

```
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(31)
<223> OTHER INFORMATION: deoxyribonucleotide

<400> SEQUENCE: 32
ggguagccgg aggagtcagt aaucggtacc c                                         31

<210> SEQ ID NO 33
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
```

```
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (27)..(31)
<223> OTHER INFORMATION: deoxyribonucleotide

<400> SEQUENCE: 33
ggguagccgg aggagtcagt aaucggtacc c                                31

<210> SEQ ID NO 34
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
```

```
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein
      is substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is
      substituted by an O-methyl group.

<400> SEQUENCE: 34
ggguagccgg aggagtcagt aaucggtacc c                              31

<210> SEQ ID NO 35
<211> LENGTH: 31
```

```
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(19)
<223> OTHER INFORMATION: ribonucleotide
<220> FEATURE:
```

```
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is
      substituted by an O-methyl group.

<400> SEQUENCE: 35
ggguagccgg aggagtcagt aaucggtacc c                              31

<210> SEQ ID NO 36
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(6)
<223> OTHER INFORMATION: deoxyribonucleotide
<220> FEATURE:
<221> NAME/KEY: misc_feature
<222> LOCATION: (7)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
```

-continued

```
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
```

```
<223> OTHER INFORMATION: When the nucleotide is a ribonucleotide, a
      hydroxyl group at the 2'-position of ribose therein is
      substituted by an O-methyl group.

<400> SEQUENCE: 36
ggguagccgg aggagtcagt aaucggtacc c                                     31

<210> SEQ ID NO 37
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide
```

-continued

```
      is a ribonucleotide, a  hydroxyl group at the 2'-position
      of ribose therein is  substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is
      substituted by an O-methyl group.

<400> SEQUENCE: 37
ggguagccgg aggagtcagt aaucggtacc c                                          31

<210> SEQ ID NO 38
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
```

<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is
      substituted by an O-methyl group.

<400> SEQUENCE: 38
ggguagccgg aggagtcagt aaucggtacc c                           31

<210> SEQ ID NO 39
<211> LENGTH: 31

-continued

```
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(19)
<223> OTHER INFORMATION: ribonucleotide
<220> FEATURE:
```

```
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (22)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is
      substituted by an O-methyl group.

<400> SEQUENCE: 39
ggguagccgg aggagtcagt aaucggtacc c                              31

<210> SEQ ID NO 40
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
```

```
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is
      substituted by an O-methyl group.

<400> SEQUENCE: 40
ggguagccgg aggagtcagt aaucggtacc c                                    31

<210> SEQ ID NO 41
<211> LENGTH: 31
<212> TYPE: DNA
<213> ORGANISM: Artificial Sequence
<220> FEATURE:
```

```
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
```

```
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is
      substituted by an O-methyl group.

<400> SEQUENCE: 41
ggguagccgg aggagtcagt aaucggtacc c                                31

<210> SEQ ID NO 42
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
```

```
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is
      substituted by an O-methyl group.

<400> SEQUENCE: 42
ggguagccgg aggagtcagt aaucggtacc c                               31

<210> SEQ ID NO 43
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
```

```
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is
      substituted by an O-methyl group.

<400> SEQUENCE: 43
ggguagccgg aggagtcagt aaucggtacc c                                       31

<210> SEQ ID NO 44
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
```

```
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
```

```
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is
      substituted by an O-methyl group.

<400> SEQUENCE: 44
ggguagccgg aggagtcagt aaucggtacc c                               31

<210> SEQ ID NO 45
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
```

<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 45
ggguagccgg aggagtcagt aaucgguacc c                          31

<210> SEQ ID NO 46
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.

```
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 46
ggguagccgg aggagtcagt aaucgguacc c                              31

<210> SEQ ID NO 47
```

```
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
```

<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 47
ggguagccgg aggagtcagt aaucgguacc c                                   31

<210> SEQ ID NO 48
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)

```
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 48
ggguagccgg aggagtcagt aaucgguacc c                                     31

<210> SEQ ID NO 49
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
```

```
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 49
ggguagccgg aggagtcagt aaucgguacc c                                   31

<210> SEQ ID NO 50
<211> LENGTH: 33
<212> TYPE: RNA
```

<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (3)..(5)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (8)..(9)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (24)..(25)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (32)..(33)
<223> OTHER INFORMATION: When the nucleotide is a ribonucleotide, a
      hydroxyl group at the 2'-position of ribose therein is
      substituted by a fluorine atom.

<400> SEQUENCE: 50
ggucuagccg gaggagucag uaaucgguag acc                                    33

<210> SEQ ID NO 51
<211> LENGTH: 33
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: deoxyribonucleotide
<220> FEATURE:
<221> NAME/KEY: misc_feature
<222> LOCATION: (5)..(29)
<223> OTHER INFORMATION: ribonucleotide
<220> FEATURE:
<221> NAME/KEY: misc_feature
<222> LOCATION: (5)..(5)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (8)..(9)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature

```
-continued

<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (24)..(25)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (30)..(33)
<223> OTHER INFORMATION: deoxyribonucleotide

<400> SEQUENCE: 51
gggguagccg gaggagucag uaaucgguac ccc                                   33

<210> SEQ ID NO 52
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide,
      hydroxyl group at the 2'-position of ribose therein is
```

```
         substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 52
ggguagccgg aggagtcagt aaucgguacc c                                    31

<210> SEQ ID NO 53
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
```

```
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is
```

```
      substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 53
ggguagccgg aggagtcagt aaucgguacc c                                31

<210> SEQ ID NO 54
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
```

```
<222> LOCATION: (13)..(14)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 54
ggguagccgg aggagucagu aaucgguacc c                                      31

<210> SEQ ID NO 55
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is
      substituted by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
```

```
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide
```

<400> SEQUENCE: 55
ggguagccgg aggagtcagt gaucgguacc c                           31

<210> SEQ ID NO 56
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
     hydroxyl group at the 2'-position of ribose therein is substituted
     by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
     hydroxyl group at the 2'-position of ribose therein is substituted
     by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
     hydroxyl group at the 2'-position of ribose therein is substituted
     by an O-methyl group.
<220> FEATURE:
<221> NAME/KEY: misc_feature
<222> LOCATION: (11)..(11)
<223> OTHER INFORMATION: When the nucleotide is a ribonucleotide, a
     hydroxyl group at the 2'-position of ribose therein is
     substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
     hydroxyl group at the 2'-position of ribose therein is substituted
     by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:

<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 56
ggguagccgg aggagtcagt aaucgguacc c                                    31

<210> SEQ ID NO 57
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.

```
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
```

<223> OTHER INFORMATION: deoxyribonucleotide

<400> SEQUENCE: 57
ggguagccgg aggagtcagt aaucgguacc c            31

<210> SEQ ID NO 58
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (12)..(12)
<223> OTHER INFORMATION: Nucleotide is phosphorothioated.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide

```
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 58
ggguagccgg aggagtcagt aaucgguacc c                                31

<210> SEQ ID NO 59
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
```

```
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
```

<222> LOCATION: (28)..(31)
<223> OTHER INFORMATION: When the nucleotide is a ribonucleotide, a
     hydroxyl group at the 2'-position of ribose therein is substituted
     by an O-methyl group.

<400> SEQUENCE: 59
ggguagccgg aggagtcagt aaucgguacc c                                31

<210> SEQ ID NO 60
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
     hydroxyl group at the 2'-position of ribose therein is substituted
     by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
     hydroxyl group at the 2'-position of ribose therein is substituted
     by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
     hydroxyl group at the 2'-position of ribose therein is substituted
     by an O-methyl group.
<220> FEATURE:
<221> NAME/KEY: misc_feature
<222> LOCATION: (11)..(11)
<223> OTHER INFORMATION: When the nucleotide is a ribonucleotide, a
     hydroxyl group at the 2'-position of ribose therein is
     substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
     hydroxyl group at the 2'-position of ribose therein is substituted
     by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
     hydroxyl group at the 2'-position of ribose therein is

```
               substituted by a fluorine atom.
<220> FEATURE:
<221> NAME/KEY: misc_feature
<222> LOCATION: (19)..(19)
<223> OTHER INFORMATION: When the nucleotide is a ribonucleotide, a
               hydroxyl group at the 2'-position of ribose therein is substituted
               by an O-methyl group.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
               hydroxyl group at the 2'-position of ribose therein is substituted
               by an O-methyl group.
<220> FEATURE:
<221> NAME/KEY: misc_feature
<222> LOCATION: (27)..(27)
<223> OTHER INFORMATION: When the nucleotide is a ribonucleotide, a
               hydroxyl group at the 2'-position of ribose therein is
               substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
               hydroxyl group at the 2'-position of ribose therein is substituted
               by an O-methyl group.

<400> SEQUENCE: 60
ggguagccgg aggagtcagt aaucgguacc c                                    31

<210> SEQ ID NO 61
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
               hydroxyl group at the 2'-position of ribose therein is substituted
               by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
               hydroxyl group at the 2'-position of ribose therein is substituted
               by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
```

<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 61
ggguagccgg aggagtcagt aaucgguacc c                               31

<210> SEQ ID NO 62
<211> LENGTH: 31
<212> TYPE: DNA
<213> ORGANISM: Artificial Sequence
<220> FEATURE:

```
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
```

-continued

```
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 62
ggguagccgg aggagtcagt aaucgguacc c                                    31

<210> SEQ ID NO 63
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
```

```
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 63
ggguagccgg aggagtcagt aaucgguacc c                                    31

<210> SEQ ID NO 64
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
```

```
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 64
ggguagccgg aggagtcagt aaucgguacc c                                    31

<210> SEQ ID NO 65
<211> LENGTH: 31
<212> TYPE: DNA
<213> ORGANISM: Artificial Sequence
<220> FEATURE:
```

```
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 65
ggguagccgg aggagtcagt aaucgguacc c                              31
```

```
<210> SEQ ID NO 66
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
```

```
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 66
ggguagccgg aggagtcagt aaucgguacc c                                   31

<210> SEQ ID NO 67
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
```

```
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 67
ggguagccgg aggagtcagt aaucgguacc c                               31

<210> SEQ ID NO 68
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(27)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
```

```
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
      hydroxyl group at the 2'-position of ribose therein is substituted
      by an O-methyl group.

<400> SEQUENCE: 68
ggguagccgg aggagucagu aaucgguacc c                                 31

<210> SEQ ID NO 69
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
```

```
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 69
ggguagccgg aggagucagu aaucgguacc c                                       31

<210> SEQ ID NO 70
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
```

```
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
```

-continued

```
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 70
ggguagccgg aggagucagu aaucgguacc c                                         31

<210> SEQ ID NO 71
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
```

<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 71
ggguagccgg aggagucagu aaucgguacc c                                    31

<210> SEQ ID NO 72
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.

```
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 72
ggguagccgg aggagucagu aaucgguacc c                              31

<210> SEQ ID NO 73
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
```

```
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 73
ggguagccgg aggagucagu aaucgguacc c                                    31

<210> SEQ ID NO 74
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl
      group.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
```

```
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 74
ggguagccgg aggagtcagt aaucgguacc c                                  31

<210> SEQ ID NO 75
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(15)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
```

```
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 75
ggguagccgg aggagtcagt aaucgguacc c                                31

<210> SEQ ID NO 76
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
```

```
        by an O-methyl group.
<220> FEATURE:
<221> NAME/KEY: misc_feature
<222> LOCATION: (7)..(8)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(27)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (11)..(11)
<223> OTHER INFORMATION: When the nucleotide is a ribonucleotide, a
        hydroxyl group at the 2'-position of ribose therein is
        substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (16)..(18)
<223> OTHER INFORMATION: When the nucleotide is a ribonucleotide, a
        hydroxyl group at the 2'-position of ribose therein is
        substituted by a fluorine atom.
<220> FEATURE:
<221> NAME/KEY: misc_feature
<222> LOCATION: (20)..(20)
<223> OTHER INFORMATION: When the nucleotide is a ribonucleotide, a
        hydroxyl group at the 2'-position of ribose therein is
        substituted by a fluorine atom.
<220> FEATURE:
<221> NAME/KEY: misc_feature
<222> LOCATION: (21)..(26)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (27)..(27)
<223> OTHER INFORMATION: When the nucleotide is a ribonucleotide, a
        hydroxyl group at the 2'-position of ribose therein is
        substituted by a fluorine atom.
<220> FEATURE:
<221> NAME/KEY: misc_feature
<222> LOCATION: (28)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
        hydroxyl group at the 2'-position of ribose therein is substituted
        by an O-methyl group.

<400> SEQUENCE: 76
ggguagccgg aggagucagu aaucgguacc c                                    31

<210> SEQ ID NO 77
<211> LENGTH: 31
```

```
-continued

<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(27)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
      hydroxyl group at the 2'-position of ribose therein is substituted
      by an O-methyl group.

<400> SEQUENCE: 77
```
ggguagccgg aggagucagu aaucgguacc c     31

```
<210> SEQ ID NO 78
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.
```

<400> SEQUENCE: 78
ggguagccgg aggagtcagt aaucgguacc c    31

<210> SEQ ID NO 79
<211> LENGTH: 31
<212> TYPE: RNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 79
ggguagccgg aggagucagu aaucgguacc c    31

<210> SEQ ID NO 80
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)

```
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(27)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
      hydroxyl group at the 2'-position of ribose therein is substituted
      by an O-methyl group.

<400> SEQUENCE: 80
``` gggguagccgg aggagucagu aaucgguacc c        31

<210> SEQ ID NO 81
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:

```
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 81
ggguagccgg aggagtcagt aaucgguacc c                                    31

<210> SEQ ID NO 82
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
```

<222> LOCATION: (17)..(18)
<223> OTHER INFORMATION: When the nucleotide is a ribonucleotide, a
       hydroxyl group at the 2'-position of ribose therein is
       substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
       hydroxyl group at the 2'-position of ribose therein is substituted
       by an O-methyl group.

<400> SEQUENCE: 82
ggguagccgg aggagtcagt aaucgguacc c                          31

<210> SEQ ID NO 83
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (13)..(14)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:

```
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 83
ggguagccgg aggagucagu aaucgguacc c                              31

<210> SEQ ID NO 84
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
```

```
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 84
ggguagccgg aggagucagu aaucgguacc c                                  31

<210> SEQ ID NO 85
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
```

```
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 85
ggguagccgg aggagucagu aaucgguacc c                                31

<210> SEQ ID NO 86
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
```

<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 86
ggguagccgg aggagtcagt gaucgguacc c                                31

<210> SEQ ID NO 87
<211> LENGTH: 31
<212> TYPE: DNA

```
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
```

<220> FEATURE:
<221> NAME/KEY: misc_feature
<222> LOCATION: (22)..(31)
<223> OTHER INFORMATION: When the nucleotide is a ribonucleotide, a
      hydroxyl group at the 2'-position of ribose therein is substituted
      by an O-methyl group.

<400> SEQUENCE: 87
ggguagccgg aggagtcagt gaucgguacc c                                  31

<210> SEQ ID NO 88
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is

```
                  substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (22)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 88
ggguagccgg aggagucagu gaucgguacc c                                    31

<210> SEQ ID NO 89
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
```

```
       hydroxyl group at the 2'-position of ribose therein is substituted
       by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (18)..(18)
<223> OTHER INFORMATION: When the nucleotide is a ribonucleotide, a
       hydroxyl group at the 2'-position of ribose therein is
       substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (22)..(31)
<223> OTHER INFORMATION: When the nucleotide is a ribonucleotide, a
       hydroxyl group at the 2'-position of ribose therein is substituted
       by an O-methyl group.

<400> SEQUENCE: 89
ggguagccgg aggagtcagt aaucgguacc c                                     31

<210> SEQ ID NO 90
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (9)..(9)
```

```
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (23)..(31)
<223> OTHER INFORMATION: When the nucleotide is a ribonucleotide, a
      hydroxyl group at the 2'-position of ribose therein is substituted
      by an O-methyl group.

<400> SEQUENCE: 90
ggguagccgg aggagtcagt aaucgguacc c                                31

<210> SEQ ID NO 91
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
```

-continued

```
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (23)..(31)
<223> OTHER INFORMATION: When the nucleotide is a ribonucleotide, a
      hydroxyl group at the 2'-position of ribose therein is substituted
``` by an O-methyl group.

<400> SEQUENCE: 91
ggguagccgg aggagtcagt aaucgguacc c                                      31

<210> SEQ ID NO 92
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (22)..(26)
<223> OTHER INFORMATION: When the nucleotide is a ribonucleotide, a
      hydroxyl group at the 2'-position of ribose therein is substituted
      by an O-methyl group.

```
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 92
ggguagccgg aggagucagu aaucgguacc c                                  31

<210> SEQ ID NO 93
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
```

```
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 93
ggguagccgg aggagucagu aaucgguacc c                                31

<210> SEQ ID NO 94
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
``` hydroxyl group at the 2'-position of ribose therein is substituted
by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
hydroxyl group at the 2'-position of ribose therein is
substituted by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
hydroxyl group at the 2'-position of ribose therein is
substituted by a fluorine atom.
<220> FEATURE:
<221> NAME/KEY: misc_feature
<222> LOCATION: (23)..(26)
<223> OTHER INFORMATION: When the nucleotide is a ribonucleotide, a
hydroxyl group at the 2'-position of ribose therein is substituted
by an O-methyl group.
<220> FEATURE:
<221> NAME/KEY: misc_feature
<222> LOCATION: (27)..(27)
<223> OTHER INFORMATION: When the nucleotide is a ribonucleotide, a
hydroxyl group at the 2'-position of ribose therein is
substituted by a fluorine atom.
<220> FEATURE:
<221> NAME/KEY: misc_feature
<222> LOCATION: (28)..(31)
<223> OTHER INFORMATION: When the nucleotide is a ribonucleotide, a
hydroxyl group at the 2'-position of ribose therein is substituted
by an O-methyl group.

<400> SEQUENCE: 94
ggguagccgg aggagucagu aaucgguacc c                              31

<210> SEQ ID NO 95
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
hydroxyl group at the 2'-position of ribose therein is substituted
by an O-methyl group.
<220> FEATURE:
<221> NAME/KEY: misc_feature
<222> LOCATION: (5)..(6)
<223> OTHER INFORMATION: ribonucleotide or deoxyribonucleotide
<220> FEATURE:
<221> NAME/KEY: misc_feature
<222> LOCATION: (6)..(6)
<223> OTHER INFORMATION: Nucleotide is non-modified or
phosphorothioated, or when the nucleotide is a ribonucleotide, a
hydroxyl group at the 2'-position of ribose therein is substituted
by a fluorine atom.
<220> FEATURE:
<221> NAME/KEY: misc_feature
<222> LOCATION: (7)..(8)
<223> OTHER INFORMATION: ribonucleotide
<220> FEATURE:
<221> NAME/KEY: misc_feature

```
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: ribonucleotide or deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: ribonucleotide or deoxyribonucleotide
<220> FEATURE:
<221> NAME/KEY: misc_feature
<222> LOCATION: (11)..(11)
<223> OTHER INFORMATION: Nucleotide is non-modified, or when the
      nucleotide is a ribonucleotide, a hydroxyl group at the 2'-
      position of ribose therein is substituted by a fluorine atom or an
      O-methyl group.
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (12)..(12)
<223> OTHER INFORMATION: Nucleotide is non-modified or
      phosphorothioated.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is non-modified or
      phosphorothioated.
<220> FEATURE:
<221> NAME/KEY: misc_feature
<222> LOCATION: (16)..(16)
<223> OTHER INFORMATION: ribonucleotide or deoxyribonucleotide
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (16)..(16)
<223> OTHER INFORMATION: a ribonucleotide wherein the base is uracil, a
      deoxyribonucleotide wherein the base is uracil or a
      deoxyribonucleotide wherein the base is thymine
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (18)..(18)
<223> OTHER INFORMATION: ribonucleotide or deoxyribonucleotide
```

```
-continued

<220> FEATURE:
<221> NAME/KEY: misc_feature
<222> LOCATION: (18)..(18)
<223> OTHER INFORMATION: Nucleotide is non-modified, or when the
      nucleotide is a ribonucleotide, a hydroxyl group at the 2'-
      position of ribose therein is substituted by a fluorine atom.
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (19)..(19)
<223> OTHER INFORMATION: ucleotide is non-modified or phosphorothioated,
      or when the nucleotide is a ribonucleotide, a hydroxyl group at
      the 2'-position of ribose therein is substituted by an O-methyl
      group.
<220> FEATURE:
<221> NAME/KEY: misc_feature
<222> LOCATION: (20)..(20)
<223> OTHER INFORMATION: ribonucleotide or deoxyribonucleotide
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: a ribonucleotide wherein the base is uracil, a
      deoxyribonucleotide wherein the base is uracil or a
      deoxyribonucleotide wherein the base is thymine
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: The base is adenine or guanine.
<220> FEATURE:
<221> NAME/KEY: misc_feature
<222> LOCATION: (21)..(22)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (22)..(22)
<223> OTHER INFORMATION: ribonucleotide or deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(31)
<223> OTHER INFORMATION: ribonucleotide or deoxyribonucleotide
<220> FEATURE:
<221> NAME/KEY: misc_feature
<222> LOCATION: (27)..(27)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (27)..(27)
<223> OTHER INFORMATION: a ribonucleotide wherein the base is uracil, a
      deoxyribonucleotide wherein the base is uracil or a
      deoxyribonucleotide wherein the base is thymine
<220> FEATURE:
<221> NAME/KEY: misc_feature
```

```
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 95
ggguagccgg aggagncagn raucgguacc c                                      31

<210> SEQ ID NO 96
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: ribonucleotide or deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is non-modified or
      phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: Nucleotide is non-modified, or when the
      nucleotide is a ribonucleotide, a hydroxyl group at the 2'-
      position of ribose therein is substituted by a fluorine atom or
      an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is non-modified or
      phosphorothioated.
<220> FEATURE:
<221> NAME/KEY: misc_feature
```

-continued

```
<222> LOCATION: (16)..(16)
<223> OTHER INFORMATION: ribonucleotide or deoxyribonucleotide
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (16)..(16)
<223> OTHER INFORMATION: The base is uracil or thymine.
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (18)..(18)
<223> OTHER INFORMATION: Nucleotide is non-modified, or when the
      nucleotide is a ribonucleotide, a hydroxyl group at the 2'-
      position of ribose therein is substituted by a fluorine atom.
<220> FEATURE:
<221> NAME/KEY: misc_feature
<222> LOCATION: (19)..(19)
<223> OTHER INFORMATION: Nucleotide is non-modified or
      phosphorothioated.
<220> FEATURE:
<221> NAME/KEY: misc_feature
<222> LOCATION: (20)..(20)
<223> OTHER INFORMATION: ribonucleotide or deoxyribonucleotide
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: The base is uracil or thymine.
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(21)
<223> OTHER INFORMATION: The base is adenine or guanine.
<220> FEATURE:
<221> NAME/KEY: misc_feature
<222> LOCATION: (21)..(22)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.
```

```
<220> FEATURE:
<221> NAME/KEY: misc_feature
<222> LOCATION: (29)..(31)
<223> OTHER INFORMATION: ribonucleotide or deoxyribonucleotide

<400> SEQUENCE: 96
ggguagccgg aggagncagn raucgguacc c                              31

<210> SEQ ID NO 97
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(6)
<223> OTHER INFORMATION: ribonucleotide or deoxyribonucleotode
<220> FEATURE:
<221> NAME/KEY: misc_feature
<222> LOCATION: (6)..(6)
<223> OTHER INFORMATION: Nucleotide is non-modified or
      phosphorothioated, or when the nucleotide is a ribonucleotide,
      a hydroxyl group at the 2'-position of ribose therein is
      substituted by a fluorine atom.
<220> FEATURE:
<221> NAME/KEY: misc_feature
<222> LOCATION: (7)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: ribonucleotide or deoxyribonucleotode
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: ribonucleotide or deoxyribonucleotode
<220> FEATURE:
<221> NAME/KEY: misc_feature
<222> LOCATION: (11)..(11)
<223> OTHER INFORMATION: Nucleotide is non-modified, or when the
      nucleotide is a ribonucleotide, a hydroxyl group at the 2'-
      position of ribose therein is substituted by a fluorine atom.
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
```

-continued

```
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: ribonucleotide or deoxyribonucleotode
<220> FEATURE:
<221> NAME/KEY: misc_feature
<222> LOCATION: (16)..(17)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (16)..(16)
<223> OTHER INFORMATION: The base is uracil or thymine.
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (18)..(18)
<223> OTHER INFORMATION: ribonucleotide or deoxyribonucleotode
<220> FEATURE:
<221> NAME/KEY: misc_feature
<222> LOCATION: (18)..(18)
<223> OTHER INFORMATION: Nucleotide is non-modified, or when the
      nucleotide is a ribonucleotide, a hydroxyl group at the 2'-
      position of ribose therein is substituted by a fluorine atom.
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (20)..(20)
<223> OTHER INFORMATION: ribonucleotide or deoxyribonucleotode
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: The base is uracil or thymine.
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(22)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (22)..(22)
<223> OTHER INFORMATION: ribonucleotide or deoxyribonucleotode
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(31)
<223> OTHER INFORMATION: ribonucleotide or deoxyribonucleotode
<220> FEATURE:
<221> NAME/KEY: misc_feature
<222> LOCATION: (27)..(27)
```

```
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (27)..(27)
<223> OTHER INFORMATION: The base is uracil or thymine.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 97
ggguagccgg aggagncagn aaucggnacc c                                          31

<210> SEQ ID NO 98
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: ribonucleotide or deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is non-modified or
      phosphorothioated.
<220> FEATURE:
<221> NAME/KEY: misc_feature
<222> LOCATION: (7)..(8)
<223> OTHER INFORMATION: When the nucleotide is a ribonucleotide,
      a hydroxyl group at the 2'-position of ribose therein is
      substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (12)..(12)
<223> OTHER INFORMATION: Nucleotide is non-modified or
      phosphorothioated.
```

```
-continued

<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is non-modified or
      phosphorothioated.
<220> FEATURE:
<221> NAME/KEY: misc_feature
<222> LOCATION: (16)..(16)
<223> OTHER INFORMATION: ribonucleotide or deoxyribonucleotide
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (16)..(16)
<223> OTHER INFORMATION: The base is uracil or thymine.
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (19)..(19)
<223> OTHER INFORMATION: Nucleotide is non-modified or
      phosphorothioated, or when the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (20)..(20)
<223> OTHER INFORMATION: ribonucleotide or deoxyribonucleotide
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is
      substituted by a fluorine atom.
<220> FEATURE:
<221> NAME/KEY: misc_feature
<222> LOCATION: (20)..(20)
<223> OTHER INFORMATION: The base is uracil or thymine.
<220> FEATURE:
<221> NAME/KEY: misc_feature
<222> LOCATION: (21)..(27)
<223> OTHER INFORMATION: ribonucleotide
<220> FEATURE:
<221> NAME/KEY: misc_feature
<222> LOCATION: (21)..(21)
<223> OTHER INFORMATION: The base is adenine or guanine.
<220> FEATURE:
<221> NAME/KEY: misc_feature
<222> LOCATION: (21)..(22)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (23)..(26)
```

```
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (28)..(31)
<223> OTHER INFORMATION: ribonucleotide or deoxyribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 98
ggguagccgg aggagncagn raucgguacc c                                    31

<210> SEQ ID NO 99
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(3)
<223> OTHER INFORMATION: Nucleotide is modified with Locked Nucleic Acid
      (LNA), or when the nucleotide is a ribonucleotide, a hydroxyl
      group at the 2'-position of ribose therein is substituted by an
      O-methyl group.
<220> FEATURE:
<221> NAME/KEY: misc_feature
<222> LOCATION: (4)..(4)
<223> OTHER INFORMATION: A hydroxyl group at the 2'-position of
      ribose in the nucleotide is
      substituted by a fluorine atom.
<220> FEATURE:
<221> NAME/KEY: misc_feature
<222> LOCATION: (6)..(6)
<223> OTHER INFORMATION: When nucleotide is a ribonucleotide, it is
      phosphorothioated.
<220> FEATURE:
<221> NAME/KEY: misc_feature
<222> LOCATION: (7)..(8)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (9)..(9)
<223> OTHER INFORMATION: ribonucleotide or deoxyribonucleotide
<220> FEATURE:
<221> NAME/KEY: misc_feature
<222> LOCATION: (9)..(9)
<223> OTHER INFORMATION: When nucleotide is a ribonucleotide, it is
      phosphorothioated.
<220> FEATURE:
<221> NAME/KEY: misc_feature
<222> LOCATION: (10)..(28)
<223> OTHER INFORMATION: ribonucleotide
<220> FEATURE:
<221> NAME/KEY: misc_feature
<222> LOCATION: (10)..(10)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
```

```
<222> LOCATION: (16)..(17)
<223> OTHER INFORMATION: A hydroxyl group at the 2'-position of
      ribose in the nucleotide is substituted by a fluorine atom.
<220> FEATURE:
<221> NAME/KEY: misc_feature
<222> LOCATION: (20)..(20)
<223> OTHER INFORMATION: A hydroxyl group at the 2'-position of
      ribose in the nucleotide is substituted by a fluorine atom.
<220> FEATURE:
<221> NAME/KEY: misc_feature
<222> LOCATION: (23)..(24)
<223> OTHER INFORMATION: A hydroxyl group at the 2'-position of
      ribose in the nucleotide is substituted by a fluorine atom.
<220> FEATURE:
<221> NAME/KEY: misc_feature
<222> LOCATION: (27)..(27)
<223> OTHER INFORMATION: A hydroxyl group at the 2'-position of
      ribose in the nucleotide is substituted by a fluorine atom.
<220> FEATURE:
<221> NAME/KEY: misc_feature
<222> LOCATION: (29)..(31)
<223> OTHER INFORMATION: ribonucleotide or deoxyribonucleotide
<220> FEATURE:
<221> NAME/KEY: misc_feature
<222> LOCATION: (29)..(31)
<223> OTHER INFORMATION: Nucleotide is non-modified, or modified with
      LNA.

<400> SEQUENCE: 99
ggguagccgg aggagucagu aaucgguacc c                              31
```